United States Patent [19]
Uyeo

[11] Patent Number: 4,464,299
[45] Date of Patent: Aug. 7, 1984

[54] ANTIBACTERIAL CARBAPENEM COMPOUNDS

[75] Inventor: Shoichiro Uyeo, Kyoto, Japan

[73] Assignee: Shionogi & Co., Ltd., Osaka, Japan

[21] Appl. No.: 370,260

[22] Filed: Apr. 20, 1982

[30] Foreign Application Priority Data

Apr. 24, 1981 [JP] Japan ................................. 56-62784

[51] Int. Cl.³ ..................... A61K 31/40; C07G 487/04
[52] U.S. Cl. ....................... 260/245.2 T; 260/245.2 R; 260/239 A; 424/270; 424/274
[58] Field of Search ................. 260/245.2 T, 245.2 R; 424/270, 271

[56] References Cited

U.S. PATENT DOCUMENTS

| 4,292,241 | 9/1981 | Tanaka et al. | 260/245.2 T |
| 4,309,346 | 1/1982 | Christensen et al. | 260/245.2 T |
| 4,347,368 | 8/1982 | Christensen et al. | 260/245.2 T |
| 4,362,665 | 12/1982 | Tanaka et al. | 260/245.2 T |
| 4,387,052 | 6/1983 | Tanaka et al. | 260/245.2 T |

*Primary Examiner*—Nicholas S. Rizzo
*Attorney, Agent, or Firm*—Wenderoth, Lind & Ponack

[57] ABSTRACT

Antibacterial carbapenem compounds represented by the general formula

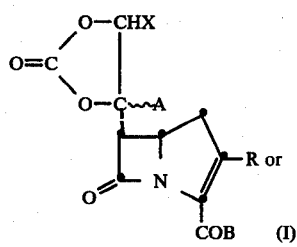

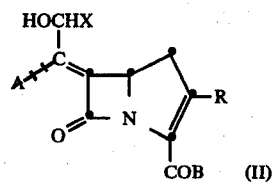

wherein X is hydrogen or alkyl, A is hydrogen or alkyl, R is hydrogen or a monovalent substituent and COB is carboxy, its pharmaceutically acceptable ester or its alkali metal salt are prepared from the suitably substituted monocyclic 2-azetidinone by a Wittig cyclization or carbene-insertion cyclization to give Compounds(I) or by cleaving the dioxolane ring of above Compounds(I) with a strong base e.g. DEN or DBU to give above Compounds(II). Some other alterations of COB, R and side chain structure are also disclosed.

16 Claims, No Drawings

ANTIBACTERIAL CARBAPENEM COMPOUNDS

This invention relates to a new class of azetidinone compounds.
[Compounds]

It relates more specifically to 3-substituted alkyl-2-azetidinone compounds represented by the following formula (I):

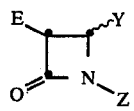

wherein
- E is optionally substituted or protected monovalent 1,2-dihydroxyalkyl in the alpha-configuration or divalent 2-hydroxyalkylidene,
- Y is hydrogen or optionally substituted alkyl, alkenyl or alkynyl,
- Z is hydrogen or optionally substituted N-protection or alkyl,
- Y and Z when combined together represent optionally substituted trimethylene or propenylene, and
- the wave line shows either the R or S bond.

Representatives of the compounds have 1,2-dihydroxyethyl or 2-hydroxyethylidene as the E group optionally substituted by methyl or optionally protected with carbonyl as cyclic carbonate or organosilyl ether. An example of the protected 1,2-dihydroxyethyl can be 2-oxo-1,3-dioxolan-4-yl optionally substituted by methyl at the 5 position and an example of the 1-hydroxyethylidene is that protected with organosilyl.

Representative Y groups include allyl, acetonyl, carboxymethyl, 2-oxo-3-carboxypropyl and 2-oxo-3-diazo-3-carboxypropyl each can optionally be protected at its carboxy. Representative Z groups include hydrogen, organosilyl and methyl optionally substituted by e.g. carboxy, protected carboxy, hydroxy, triarylphosphoranilidenne, triarylphosphonium and/or halogen. In these examples, the protection for carboxy can be one of those conventional in the field of penicillin and cephalosporin chemistry, including p-nitrobenzyl, o-nitrobenzyl, p-methoxybenzyl, acetoxymethyl, pivaloyloxymethyl, 1-ethoxycarbonyloxyethyl, phthalidyl and indanyl carboxylate esters and alkali metal carboxylate salts forms. Y and Z when combined together can represent a divalent group selected from the following structures.

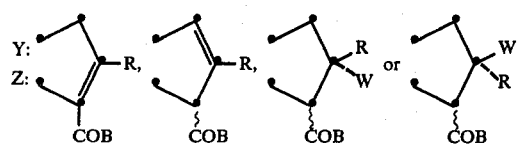

wherein
- R is hydrogen or a substituent e.g. halogen, alkylamino, hydroxy, acyloxy, alkoxy, optionally unsaturated alkylthio, aminoalkylthio, acylaminoalkylthio, alkylsulfinyl, aminoalkylsulfinyl, acylaminoalkylsulfinyl, arylthio, arylsulfinyl, heterocyclic thio, heterocyclic sulfinyl, alkylamino, amino and alkyl,
- W is hydrogen or halogen,
- R and the W when combined together represent oxo or a ketal group,
- COB is carboxy or protected carboxy, and
- wave line is as defined above.

A class of the compounds of this invention has the following general formula:

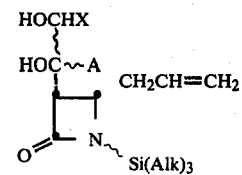

wherein
- A, Alk and X are each hydrogen or optionally substituted alkyl, and
- the wave line is as defined above.

This compound can be acylated to form the cyclic carbonate of the formula (II), another class of the compounds of the following general formula:

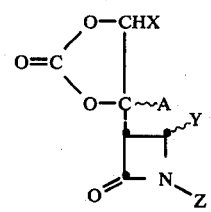

wherein
- A, X and the wave line are as defined above,
- Y is hydrogen, alkyl, alkenyl or alkynyl optionally substituted e.g. by hydroxy, acyloxy, organosilyloxy, oxo, carboxy, protected carboxy, diazo and/or acylamino, and
- Z is hydrogen, an amino-protecting group e.g. trialkylsilyl, alkoxydialkylsilyl, acyl or protected carboxymethyl optionally substituted by e.g. hydroxy, oxo, optionally substituted alkyl or alkylidene, alkylenedioxy, triarylphosphoranilidene, triarylphosphonium or halogen. A further class of compounds includes fused bicyclic carbapenem compounds (III) representable by the following formula:

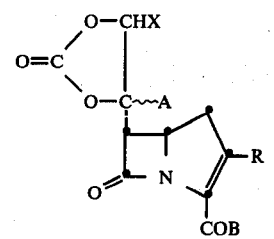

wherein A, COB, R, X and the wave line are as defined above.

Representatives of these compounds have hydrogen or methyl as A, carboxy or protected carboxy conventional in the field of beta-lactam chemistry as COB and hydrogen, methyl, methylthio, methylsulfinyl, acetamidoethylthio, acetamidoethylsulfinyl, acetamidovinylthio or acetamidovinylsulfinyl as R.

Another class of compounds (IV) belongs to so-called carbapenams and is represented by the following formula:

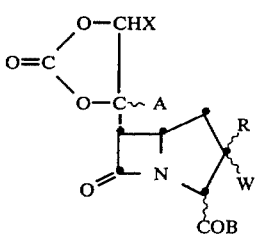
(IV)

wherein A, COB, R, W, X and the wave line are as defined above.

The last class of compounds are hydroxyalkylideneazetidinone compounds (V) of the following formula:

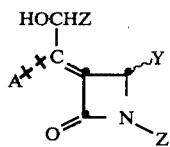
(V)

wherein A, COB, R and X are as defined above and the +++ line shows either the geometrically isomeric E or Z bond, and its O-trialkylsilylated derivatives.

The said substituents in the preceding paragraphs for each of the classes of the compounds and the general formulas can be a carbon group e.g. alkyl, alkenyl, alkylidene, aralkyl, aryl, heterocyclic group, carboxy, protected carboxy, carbamoyl, alkanoyl, aralkanoyl, aroyl or cyano, a nitrogen group e.g. amino, diazo, azido, hydrazinyl, amino, alkylamino, aralkylamino, arylamino, acylamino, alkylideneamino, acylimino, imino, alkylimino, nitro, nitroso or ammonio, an oxygen group e.g. hydroxy, alkoxy, aralkoxy, aryloxy, acyloxy or oxo, a halogen atom e.g. fluorine, chlorine, bromine or iodine, a silyl group e.g. trialkylsilyl, alkoxydialkylsilyl or aminodialkylsilyl, a phosphorus group e.g. phosphinyl, phospho, phophoranyl, phosphoranilidene or phosphonium, a sulfur group e.g. mercapto, alkylthio, arylthio, acylthio, alkylsulfinyl, arylsulfinyl, alkylsulfonyl, arylsulfonyl or thioxo, a metal atom e.g. lithium, sodium, potassium, magnesium, or calcium and other groups. Where possible, these substituents can have further substituent, unsaturated bond or heteroatom in tertiary-alkyl, benzyl or benzhydryl optionally substituted by e.g. halogen, hydroxy, alkoxy, nitro, alkyl, aryl or phthalidyl ester, symmetrical or unsymmetrical anhydride, amide, substituted hydrazide or the like i.e. carboxy modified by a carboxy protecting group conventional in the chemistry of beta-lactam antibiotics.

As clinical drugs, pharmaceutically acceptable carboxylate salts and esters of above classes are practically important. These can be a sodium, potassium or alkaline earth metal carboxylate salt or an acetoxymethyl, pivaloyloxymethyl, 1-ethoxycarbonyloxyethyl, phthalidyl, phenyl or indanyl carboxylate ester or the like.

The acyl group appeared in the preceding paragraphs can be mineral acid acyl, alkanoyl, alkoxycarbonyl, aralkoxycarbonyl, aralkanoyl, aroyl, alkylsulfonyl, arylsulfonyl or the like optionally having an unsaturated bond, substituent or hetero atom.

The said organosilyl as an O- or N-protecting group for E, Y and Z can be e.g. trialkylsilyl, dialkylalkoxysilyl, aralkyldialkylsilyl or aryldialkylsilyl.

The halogen as appearing in the preceding explanation of each group can be fluorine, chlorine, bromine or iodine.

The alkyl, alkenyl, alkanoyl or the like aliphatic group as appearing in the preceding explanation of each groups can be straight, branched, cyclic or partially cyclic.

The aromatic group e.g. aryl and heterocyclic group as appearing in the preceding explanation of each groups can have a substituent e.g. alkyl, halogen, nitro, cyano, alkanoyl, hydroxy or the like.

Among the already disclosed compounds, the following preferable compounds are more specifically listed.

Preferable azetidinone compounds (II) have A as hydrogen or 1 to 3C alkyl; X as hydrogen or 1 to 3C alkyl; Y as 1 to 5C alkyl or alkenyl optionally substituted by carboxy, protected carboxy, oxo, diazo and/or alkanoylaminovinylthiocarbonyl; Z as hydrogen, trialkylsilyl in which alkyl may be the same or different 1 to 5C alkyl, optionally protected carboxyhydroxymethyl, optionally protected carboxyhhalomethyl or optionally protected carboxytriarylphosphoranilidenemethyl in which each aryl is the same or different monocyclic aryl; and the wave line shows either R- or S-bond.

Preferable carbapenam or carbapenem compounds (III), (IV) and (V) have A as hydrogen or 1 to 3C alkyl; B as a conventional carboxy-protecting ester conventional in the beta-lactam chemistry or alkali metal or alkaline earth metal salt group or atom; R is hydrogen, hydroxy, 1 to 3C alkyl, 1 to 3C alkylthio, 1 to 3C alkylsulfinyl, 3 to 6C alkanoylaminoalkylthio, 3 to 6C alkanoylaminoalkylsulfinyl, 3 to 6C alkanoylaminoalkenylthio, 3 to 6C alkanoylaminoalkenylsulfinyl; S as hydrogen or trialkylsilyl in which eaach alkyl is the same or different 1 to 5C alkyl; W is hydrogen or halogen, X is hydrogen or 1 to 3C alkyl; R and W when combined show oxo.

Preferable carbapenem compounds (III) have A, B, R. X and wave line as defined above, in which more preferable are those having A as hydrogen or methyl; B as hydrogen, sodium, p-nitrobenzyl, o-nitroenzyl, pivaloyloxymethyl, diphenylmethyl, phthalidyl or phenyl; R as hydrogen, hydroxy, methyl, methylthio, methylsufinyl, acetylaminoethylthio, acetylaminoethylsulfinyl, acetylaminovinylthio or acetylaminovinylsulfinyl; and X as hydrogen or chlorine. Some of the specific compounds are those having R as hydrogen and B as hydroen, sodium, p-nitrobenzyl or pivaloyloxymethyl; R as methyl, B as hydrogen, sodium, p-nitrobenzyl or pivaloyloxymethyl; R as methylthio, B as hydrogen, sodium, or p-nitrobenzyl; R as methylsulfinyl and B as hydrogen, sodium, p-nitrobenzyl or diphenylmethyl; R as acetylaminoethylthio and B as hydrogen, sodium, p-nitrobenzyl or pivaloyloxymethyl; R as acetylaminoethylsulfinyl, B as hydrogen, p-nitrobenzyl or pivaloyloxymethyl; R as acetylaminovinylthio and B as hydrogen, sodium, p-nitrobenzyl or pivaloyloxymethyl; and R as acetylaminovinylsulfinyl and B as hydrogen, sodium, p-nitrobenzyl or pivaloyloxymethyl.

Preferable carbapenem compounds (V) are those having A as hydrogen or methyl, B as hydrogen, sodium, p-nitrobenzyl, o-nitrobenzyl, pivaloyloxymethyl or diphenylmethyl; R as hydrogen, methyl, methylthio, methylsulfinyl, acetylaminoethylthio, acetylaminoethylsulfinyl, acetylaminovinylthio, acetylaminovinylsulfinyl; and S as hydrogen or trimethylsilyl.

Preferable carbapenam compounds (IV) are those having R as hydrogen, ethylthio, methylsufinyl, acetylaminoethylthio, acetylaminoethylsulfinyl, acetylaminovinylthio oracetylaminovinylsulfinyl; X as hydrogen or chlorine: B as hydrogen, sodium, p-nitrobenzyl or pivaloyloxymethyl; R and X combined to show oxo.

Among the azetidinone compounds (II), preferable are those represented by the following formula

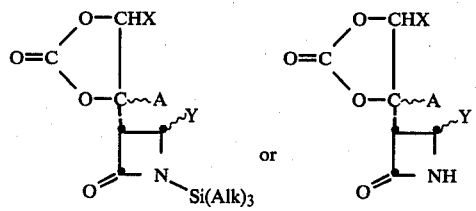

wherein A, X, Y and wave line are as defined above and Alk is 1 to 5C alkyl. Among which preferable members have A as hydrogen or methyl and Y as allyl, acetonyl, carboxymethyl, p-nitrobenzyloxycarbonylacetonyl or 3-p-nitrobenzyloxycarbonyl-3-diazo-2-oxopropyl.

Other preferable azetidinone compounds are represented by the following formula

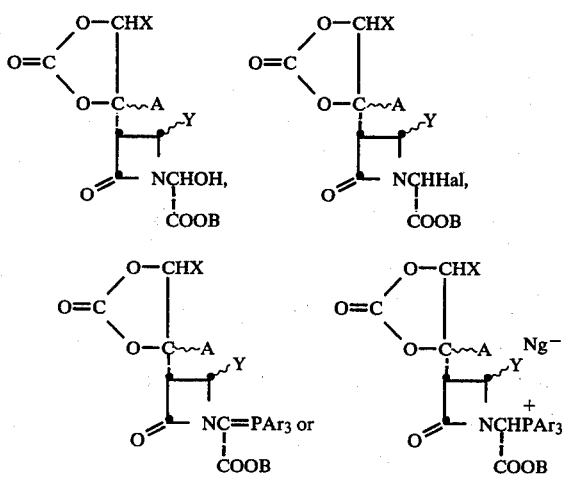

wherein A, B, COB, Hal, X, Y and wave line are as defined above, Ar is aryl and Ng is an anionic group. More specific compounds have A as hydrogen, Y as allyl, B as p-nitrobenzyl or pivaloyloxymethyl, Ar as phenyl, and Ng as halide or carboxylate; A as methyl, B as hydrogen, sodium, p-nitrobenzyl, o-nitrobenzyl or pivaloyloxymethyl, Ar as phenyl and Ng as halide or carboxylate; Y as allyl, acetonyl, acetamidovinylthiocarbonyl-methyl or carboxymethyl optionally protected with p-nitrobenzyl.

[Use]

Compounds (II) are intemediates for synthesizing Compounds (V). Compounds (IV) are intermediates for synthesizing Compounds (III). The compounds (III) and (V) having a carbapenem ring structure and COB being a carboxy or pharmaceutically acceptale salt or ester group conventional in beta-lactam chemistry, e.g. an alkali metal salt or an acyloxyalkyl, aryl or phthalidyl ester group are antibacterials and can be used as bacteriocides for the purpose of e.g. human or veterinary drugs, disinfectants or antiperishing agents. For preventing or treating infections in man caused by sensitive bacteria, about 20 mg compound per kilogram body weight is usually administered intravenously. The dose and interval of the administration can be selected according to he seriousness of infection and the resistace of bacteria to the compound.

[Prior art]

Carbapenem compounds as a group of members in the field of beta-lactam antibacterials developing rapidly in these ten years have the nucleus of the formula with the tentative position numers as given below.

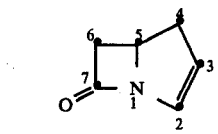

1-Azabicyclo[3.2.0]hept-2-ene nucleus

Many publications have presented these so-called carbapenem antibacterials having 1-azabicyclo[3.2.0-]heptene nucleus. The antibacterial activity largely depends on the structure of the substituent at the 6 position and modified by that of the substituent at the 3 position.

Representatives of the known substituents at the 6-position include:

Hydrogen (or no substituent) in J. American Chemical Society, 100, 8006 (1978), Japanese Patent Application Publication (Kokai) 55-112997, Ethyl in J. Antibiotics, 31, 480 (1978), Japanese Patent Application Publication (Kokai) 54-30195, Isopropyl in Japanese Patent Application Publication (Kokai) 54-76593, Hydroxyethyl in J. Antibiotics, 32, 1 (1979), J. American Chemical Society, 100, 6491 (1978), Japanese Patent Application Publication (Kokai) 54-125694, U.S. Pat. No. 4,135,978, 1-Sulfoxyethyl in J. Chemical Society, Chem. Comm. 1977, 523, 953, Japanese Patent Application Publication 54-20194, 1-Alkylthioethyl in Japanese Patent Application Publication (Kokai) 54-157595, 2-Hydroxyethylidene in Japanese Patent Application Publication (Kokai) 55-136282, Oxo in Japanese Patent Application Publication (Kokai) 55-22695, and Amino in U.S. Pat. No. 4,217,453.

Representatives of the 3-substituents include

Hydrogen (no substituent) in J. American Chemical Society, 100, 8006 (1978), Japanese Patent Application Publication (Kokai) 54-151996, Alkyl or aryl in Tetrahedron Letters 21, 2013 (1980), Japanese Patent Application Publication (Kokai) 54-66696, Alkylthio in Journal of American Chemical Society, 100, 6491 (1978), Alkenylthio in J. Antibiotics, 32, 961 (1979), Japanese Patent Application Publication (Kokai) 55-11887 and those referred to in e.g. 'Topics in Antibiotic Chemistry,' Volume III, pp. 129 (1980), John Wiley and Sons, N.Y., including the followings:

Acylaminoalkylthio in Japanese Patent Application Publication (Kokai) 54-59295,

Pyrimidylthio in Japanese Patent Application Publication 55-33494,

Acylaminoalkenylthio in J. Chem. Society, Chem. Comm., 1977, 523; Japanese Patent Application Publication (Kokai) 54-59295;

Acylaminoalkylsulfinyl: in Japanese Patent Application Publication (Kokai) 45-22695, Acylaminoalkenylsulfinyl in Japanese Patent Application Publication (Kokai) 55-136282, Amino in U.S. Pat. No. 4,217,453, Hydroxy in J. American Chemical Society, 102, 6161 (1980), and Halogen in Japanese Patent Application Publication (Kokai) 55-147284.

[Method of Synthesis]

The claimed compounds (I) to (V) of this invention can be synthesized by way of one of the methods as described in the following part of this specification.

1. Cyclization

Cyclization of a suitably substituted monocylic azetidinone compound gives a fused bicyclic azetidinone compound having the carbapenem bicyclic nuclus.

Representative cyclizations known in the art include:

A ring closure using malonate synthesis in J. Organic Chemistry, 45, 1135, 1142 (1980), Japanese Patent Application Publication (Kokai) 1959-66697;

Ring closure using aldol condensation in Tetrahedron Letters, 21, 4009 (1980), Japanese Patent Application Publication (Kokai) 1980-73682;

Ring closure using Wittig reaction: in J. Chem. Soc. Chem. Comm., 1980, 429; 1979, 236; J. American Chemical Society, 100, 8006 (1978); Japanese Patent Application Publications (Kokai) 1979-112887; 1980-69586;

Ring closure using carbenoid insertion: in Tetrahedron Letters, 21, 31 (1980), J. American Chemical Society, 102, 6161 (1980), Japanese Patent Application Publication 1980-27169; and the like.

For synthesizing carbapenem compounds (I) there is preferably used mild Wittig reaction or carbene insertion reaction. for the cyclization.

A. Cyclization using Wittig reaction

Treating a triarylphosphorane compound (1) in an inert solvent at 0° C. to 150° C. for 10 minutes to 50 hours affords the objective Compound (2):

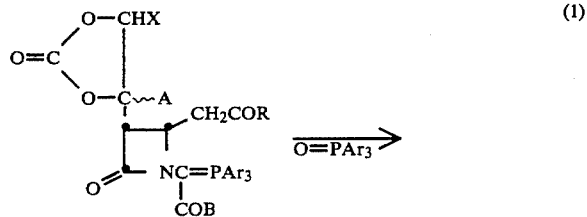

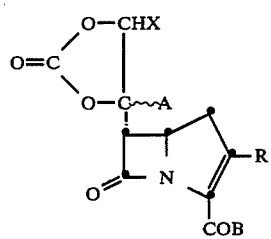

(wherein A, COB, R, X are as above and Ar is aryl)

This reaction does not require any specific reagent and it is a condensation caused by heat.

The inert solvent to be used here can be that can dissolve the starting material and have not adverse effect on the starting material, product and the reaction, e.g. hydrocarbon e.g. benzene, toluene, hexane, octane, halohydrocarbon e.g. dichloromethane, trichloroethane, chlorobenzene; ether e.g. dioxane solvents for industrial use. The reaction mixture is then concentrated, purified to remove by-products e.g. triarylphosphorane oxide, to produce the objective carbapenem compound (2) in high yield.

B. Cyclization by carbenoid insertion reaction

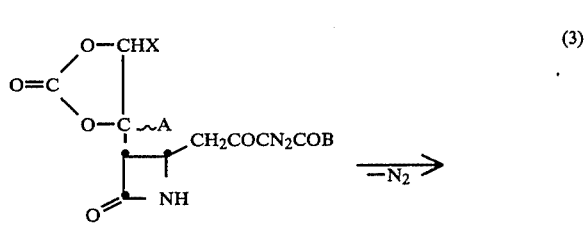

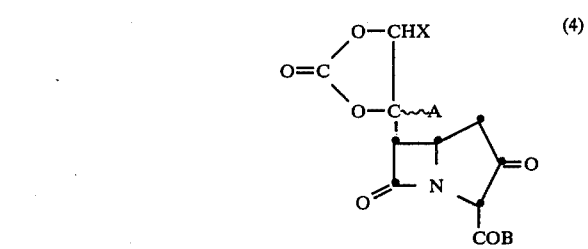

(wherein A, COB and X are as defined above)

The compound having 3-protected carboxy-3-diazo-2-oxopropyl at the 4 position (3) is kept at 50° C. to 110° C. for about 10 minutes to 5 hours in the presence of heavy metal catalyzer e.g. copper acetoacetate, copper acetate, copper sulfate, copper powder, rhodium acetate, lead acetate, in an inert solvent afford the carbapenam compound (4).

This cyclization can be also done by photo reaction of the same diazocarboxylic acid derivative by irradiating ultraviolet ray higher than 300 nm in an inert solvent in the cold to obtain the objective carbapenam compound (4).

In each case, the product can be isolated from the reaction mixture and purified by a conventional method.

C. Preparation of the starting material (1) Formation of 2-oxo-1,3-dioxolane ring.

The 2-oxodioxolane ring for this reaction can be prepared by e.g. following reactions:

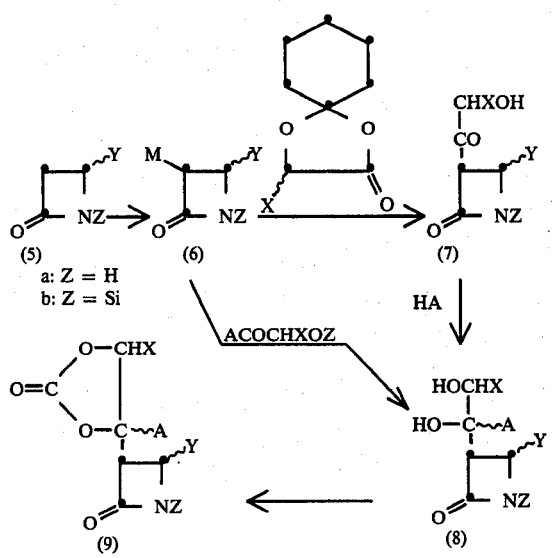

dium borohydride, in alcohol at −80° C. to 10° C. for 0.5 to 5 hours to give 3-(1,2-dioxyethyl) compound (8; A=H) or alternatively, carbonyl addition reagent e.g. Grignard reagent, alkyl alkali metal, in an inert solvent e.g. dichloromethane, ether, tetrahydrofuran, at −20° C. to 100° C. for 0.5 to 5 hours or other conventional method to give the dihydroxyalkyl compounds (8; A≠H). The same compounds can be prepared by treatment of the said metalated azetidinone compounds (6) with protected hydroxyacetyl compound $ACOCH_2OZ$ in an inert solvent e.g. tetrahydrofuran at −80° C. to 0° C. for 0.1 to 5 hours to add Compound (6) to the carbonyl of $ACOCH_2OZ$. The diol compound (8) is treated with carbonating reagent e.g. phosgene, phosgene dimer, pyrocarbonate ester, or the like in the presence of an acid scavenger e.g. diisopropylamine, triethylamine, pyridine, in an inert solvent e.g. dichloromethane, chloroform, benzene, ethyl acetate, in a conventional manner at −80° C. to 0° C. for 1 to 5 hours to give a 3-(2-oxo-1,3-dioxolanyl)-2-azetidinone compound (9).

(2) Conversion of Z attached to the 1 position

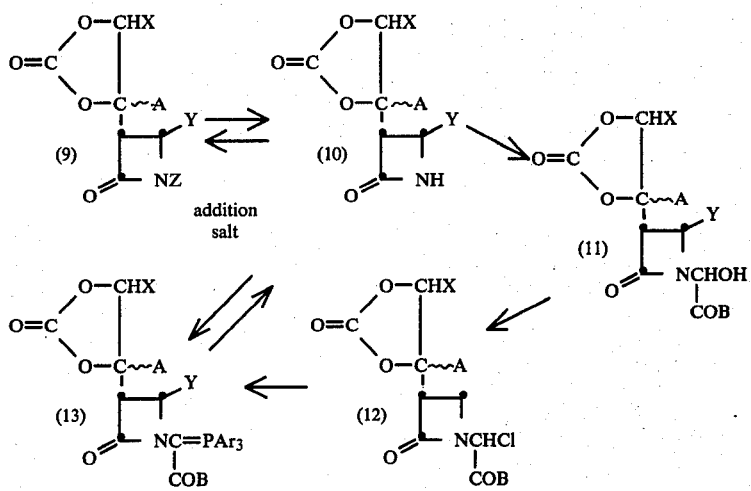

(wherein A, X, Y and Z are as defined above; and M is a light metal atom)

The 2-oxodioxolane ring can be prepared e.g. by the introduction of 1,2-dioxyethyl into 4-allyl-2-azetidinone (5a: Y=allyl) described in J. Chemical Society, Chem. Comm., 1979, 236 and carbonate formation according to the above reaction scheme. Namely, treatment of Compound (5a) with organosilyl reagent e.g. t-butyldimethylsilyl chloride, t-butyldiphenylsilylchloride, trimethylsilyl chloride, hexamethyldisilazane in an inert solvent e.g. dimethyl formamide, acetonitrile, hexamethylphosphorotriamide, dioxane, in the presence of an acid scavenger e.g. diiosopropylamine, triethylamine, pyridine, lutidine, at −20° C. to 25° C. for 0.5 to 24 hours to obtain 1-protected allyl compound (5b) and then treated with a base e.g. lithium diisopropylamide, sodium hydride, phenyllithium, butyl lithium, in an inert solvent e.g. dioxane, dimethoxyethane, tetrahydrofuran, at −80° C. to 0° C. for 1 to 5 hours to metalate to obtain 1-organosilyl-4-allyl-3-metalated-2-azetidinone (6). This is treated with 1,4-dioxaspiro[5,4]decan-2-one in an inert solvent e.g. ether, dimethoxyethane, tetrahydrofuran, at −80° C. to 0° C. for 1 to 3 hours to give a 1-organosilyl-4-allyl-3-hydroxyacetyl-2-azetidinone (7). This compound can be reduced with e.g. so- (wherein A, Ar, COB, X, Y and Z are as defined above)

The organosilyl group represented by Z can be removed by the action of acid (mineral acid, acetic acid, etc.), if required in the presence of a phase transfer reagent e.g. tetrabutylammonium bromide, in an inert solvent e.g. alcohol, tetrahydrofuran, dioxane, at 0° C. to 100° C. for 1 to 10 hours.

Introduction of the organosilyl group can be carried out analogous to the previous section (1).

By the action of glyoxylic acid or its ester on azetidinone (10) in an inert solvent e.g. N,N-dimethylformamide, tetrahydrofuran, in the presence of an acid scavenger e.g. diisopropylamine, triethylamine, picoline, affords glycolate (11).

Reaction of the glycolate (11) with a halogenating reagent e.g. thionyl chloride, phosphorus trichloride, phosphorus pentachloride, phosphorus oxychloride, oxalyl chloride, in the presence of an acid scavenger e.g. triethylamine, diisopropylamine, pyridine, at −20° C. to 40° C. for 30 minutes to 20 hours gives a haloacetate (12).

Action of triarylphosphine on haloacetate (12) in an inert solvent e.g. dioxane, tetrahydrofuran, in the presence of an acid scavenger e.g. diisopropylamine, triethylamine, pyridine, lutidine, at 0° C. to 100° C. for 1 to 50 hours give phosphorane compound (13).

Phosphorane compound (13) is treated with more than an equivalent of acid gives the corresponding phosphonium salt by reversible formation of an addition salt. This step prevents lowering of yield due to deterioration of fission at position 1 in the course of ozone oxidation.

Alternatively, chloroacetate (12) can be reacted with trimethylphosphite to produce an Emonds reagent. The latter can be used to make an intramolecular condensation in the presence of a base to make a bicyclic compound.

(3) Conversion of the Y group attached to the 4 position

Monocyclic compound (I) can be subjected to cyclization reaction by using a combination of following reactions to have Y group corresponding to the R in the objective compounds to form —CH$_2$COR for Wittig reaction or —CH$_2$COCN$_2$COB for a carbene insertion. Thus, this way provides a route from a known compound to the compound (2).

(i) When R is hydrogen

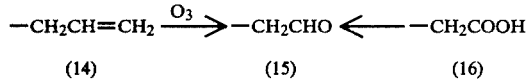

If the substituent at the 4 position is allyl (14), the compound is brought to contact with ozone in an inert solvent e.g. dichloromethane, trichloroethane, ethyl acetate, at −80° C. to 0° C. to form an ozonide, then let react with a reducing reagent e.g. dimethyl sulfide, acetic acid-zinc, according to a conventional manner to give the corresponding compound having formylmethyl at the 4 position (15).

When the substituent at the 4 position is carboxymethyl (16), the compound is preferably converted to make acid chloride or ester, treated with a reducing reagent e.g. aluminum hydride complex, alkoxyaluminum hydride compounds, palladium-barium salt catalyst in the presence of hydrogen, under conventional condition e.g. solvent, temperature, time, workup, to the corresponding formylmethyl compound (15).

(ii) When R is alkyl

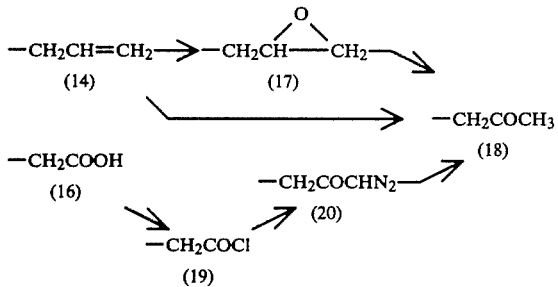

Oxidation of 4-allyl compounds (14) with e.g. percarboxylic acid, persulfonic acid, hydrogen peroxide, in an inert solvent e.g. trichloroethane, chloroform, ethyl acetate, at −30° C. to 10° C. for 1 to 5 hours affords the corresponding epoxide compound (17).

The epoxy compound (17) is treated with an acid e.g. mineral acid, sulfonic acid, in an aprotic solvent e.g. trichloroethane, ethyl acetate, at 0° C. to 50° C. to afford acetonyl compound (18).

The said 4-allyl compound (14) can also be oxidized with an oxidizing reagent e.g. mercuric acetate, cupper chloride, if required in the presence of an oxidation catalyst, in an inert solvent e.g. methanol, ethanol, at 0° C. to 70° C. for 1 to 8 hours to afford the corresponding 4-acetonyl compound (18).

Reaction of 4-carboxymethyl compound (16) with a chlorinating reagent e.g. oxalyl chloride, thionyl chloride, in the presence of an acid scavenger e.g. triethylamine, pyridine, to afford the corresponding acid chloride (19). This is treated with a diazoalkane in an inert solvent e.g. diethyl ether, tetrahydrofuran, dioxane, if required in the presence of an acid scavenger to form diazoketone (20), followed by the reductive elimination of nitrogen or like method to give 4-(2-oxoalkyl compound (18) in a conventional manner.

Similarly, analogous homologues having larger carbon number can also be prepared.

(iii) When R is thio group

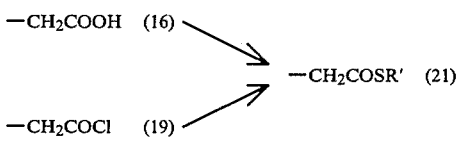

(R' is aliphatic, aromatic or heterocyclic group)

Reaction of a 4-carboxymethyl compound (16) with a desired thiol compound in an inert solvent e.g. dichloromethane, acetonitrile, if required in the presence of an accelerating reagent e.g. N,N-dimethylformamide, or of a dehydrating condensing reagent e.g. dicyclohexyl carbodiimide, 1-ethoxycarbonyl-2-ethoxy-1,2-dihydroquinoline gives the corresponding thiol ester (21) at 0° C. to 40° C. for 1 to 10 hours.

The corresponding chlorocarbonylmethyl compound (19) can be transformed to the corresponding thiol ester (21) by the reaction with a thiol compound represented by R'SH if required in the presence of a base.

The starting material of afore stated reactions, i.e. 4-allyl compound (14) can be prepared by the reactions described under the item C(1).

(iv) Other conversion of Y groups

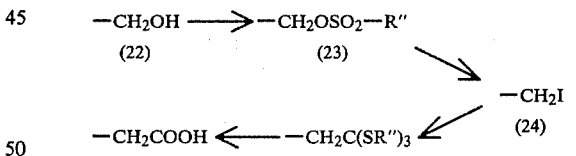

Reaction of 4-hydroxymethyl compound (22) with a sulfonylating reagent e.g. methanesulfonyl chloride, p-toluenesulfonic chloride, methanesulfonic anhydride, in the presence of an acid scavenger e.g. triethylamine, diisopropylamine, picoline, in an inert solvent e.g. dichloromethane, trichloroethane, chloroform at 0° C. to 40° C. for 30 minutes to 2 hours gives the corresponding sulfonic acid ester (23).

Obtained 4-sulfonyloxymethyl compound (23) is reacted with alkali metal iodide at 0° C. to 50° C. for 1 to 5 hours in a polar inert solvent e.g. methyl ethyl ketone, tetrahydrofuran, dioxane, gives the corresponding iodomethyl compound (24).

The iodomethyl compound (24) is treated with carbanion reagent e.g. tri-(-aliphatic or aromatic thio)methyl metal at −100° C. to 0° C. for 30 minutes to 5 hours in an inert solvent e.g. tetrahydrofuran, dioxane, dimethoxyethane to afford the corresponding orthothioester (25).

Reaction of the orthothioester (25) with a thiolester hydrolyzing reagent e.g. mercuric salts, thalium salts, tetrafluoroboric acid salts, in an polar solvent e.g. water, methanol, ethanol, isopropanol, at 0° C. to 80° C. for 1 to 30 hours gives the corresponding carboxymethyl compound (16).

The starting material, 4-hydroxymethyl compound (22) can be prepared e.g. by the method of C(1) on a compound appeared in Japanese Patent Application Publication 1980-27169.

The 4-carboxymethyl compound (16) can be prepared e.g. by the said method on 4-carboxy-2-azetidinone described in J. Am. Chem. Soc., 102, 6161 (1980).

(v) β-Oxo-diazocarboxylic acid side chain formation

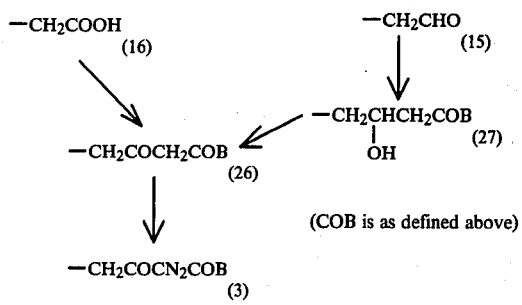

(COB is as defined above)

The carboxy of 4-carboxymethyl compound (16) is activated with a dehydrating condensing reagent e.g. N,N'-carbonyl diimidazole, 1-ethoxycarbonyl-2-ethoxy-1,2-dihydroquinoline, or like activating reagent, and then reacted with a metal salt of malonic half ester e.g. malonic p-nitrobenzyl ester magnesium salt, lithium salt, in an inert solvent e.g. benzene, toluene, tetrahydrofuran, dioxane, at 0° C. to 70° C. for 1 to 20 hours to give the protected carboxyacetonyl compound (26).

Reaction of a 4-formylmethyl compound (15) with metalated acetate ester e.g. (lithio, halomagnesio or cadminio)acetate, at −80° C. for 15 minutes to 8 hours in an inert solvent e.g. tetrahyrofuran, dioxane, dimethoxyethane, affords a β-hydroxycarboxylic acid derivative (27).

β-Hydroxycarboxylic acid (27) can be treated with an oxidizing reagent e.g. chromium trioxide compound, acid anhydride dimethyl sulfoxide mixture, hypohalite, in an inert solvent e.g. acetonitrile, dioxane, dichloromethane, at −50° C. to 50° C. for 10 minutes to 5 hours to give a protected carboxyacetonyl compound (26).

The reactions from compound (15) through compound (27) to Compound (26) can be replaced by Claisen condensation, Aldol condensation, Wittig reaction or other additions of acetic acid unit, followed by oxidation of the alcohol to give the β-oxo group. The reaction conditions can be selected from the conventional ones.

Reaction of a protected carboxyacetonyl compound (26) (I) with an aliphatic or aromatic sulfonic azide e.g. methanesulfonyl azide, ethanesulfonylazide, toluenesulfonyl azide, carboxybenzenesulfonyl azide, in an inert solvent e.g. acetonitrile, chloroform, dioxane, tetrahydrofuran, in the presence of a base e.g. diisopropylamine, triethylamine, pyridine, picoline at 0° C. to 30° C. for 30 minutes to 30 hours gives β-oxodiazocarboxylic acid (3).

2. Modification of carboxy

For the purpose of convenience for synthesis or medical use, when Compounds (I) or (II) have carboxy group as COB, the group is modified by salt formation, esterification or the like or alternatively, when they have protected carboxy as COB the protection can be removed in a conventional manner in the art of β-lactam antibacterials.

For example, carboxylic acids in an organic solvent or inorganic solvent afford the corresponding salts by mixing with an organic or inorganic base. The product can be isolated by condensing the reaction mixture, lyophilization, separation by adding a insoluble solvent or the like conventional method to recover in a solid form.

Reaction of a carboxylic acid with an esterifying reagent e.g. p-nitrobenzyl bromide, cyclopropylmethyl chloride, pivaloyloxymethyl iodide, acetoxymethyl iodide, ethoxycarbonyloxyethyl iodide, in the presence of an acid scavenger e.g. triethylamine, picoline, at a temperature of −20° C. to 30° C. for a duration of 1 hour to 5 hours gives the corresponding ester. Other carboxy protections include other esters, amides, hydrazides, acid anhydrides, each can be produced by a conventional method in the art.

A protected carboxy can be deprotected to afford carboxy by a conventional method in the art for the specific protection. For example, β-haloalkyl ester can be removed by reductive fission, elimination of isobutene from a t-butyl ester with acid, hydrogenolysis or Lewis acid elimination of aralkyl ester or base treatment of alkyl or aralkyl esters.

Due to instability of compounds (I) and (II), each treatment is preferably done under a mild condition.

These methods in this section may be done according to one of described reactions and reaction conditions e.g. those appeared in McOmie "Protective Groups in Organic Chemistry", Plenum Press, London (1973), pp. 183.

3. Addition

Reaction of a carbapenem compound (2) with an addition reagent HR affords the corresponding carbapenam compound (27).

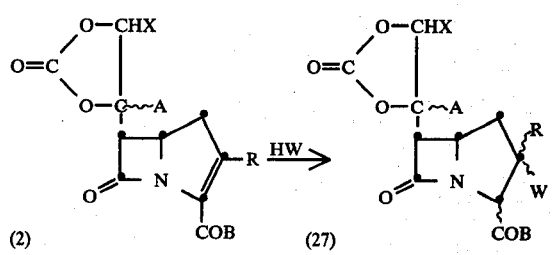

(wherein A, COB, R, W, X and wave line are as defined above).

The addition reagent includes hydrogen, mercaptanes and the like. When mercaptane is an addition reagent, a base e.g. triethylamine, alkali metal carbonate can be added as an accelerator, and when hydrogen is the addition reagent, hydrogenation catalyst (e.g. platinum, palladium, nickel, can be an accelerator. These reactions can be carried out in an inert solvent e.g. tetrahydrofuran, dioxane, alcohol, acetonitrile, ethyl acetate, at 0° C. to 100° C. for 1 to 5 hours by contacting the starting material and reagent.

These reactions can be carried out under the conditions analogous to those appearing in J. Chemical Society, Chem. Comm. 1980, 185, Japanese Patent Application Publication (Kokai) 1979-76593; 1979-151996; 1980-20194; 1980-73681.

4. Introduction of a double bond by an elimination

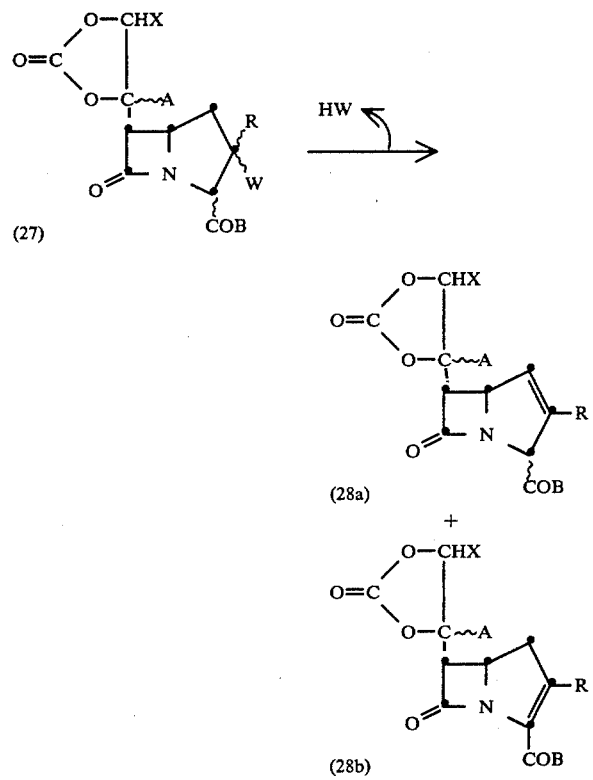

(wherein A, COB, R, W, X and wave line are as defined above)

When the group W of the carbapenem compound (27) is halogen, a treatment with a base e.g. triethylamine, DBN, DBU in an inert solvent e.g. acetonitrile, chloroform, trichloroethane, at a temperature of $-10°$ C. to 50° C. for 1 to 5 hours gives carbapenem compound (28a) or (28b) on the elimination of hydrogen halide.

When the group R is aliphatic or aromatic sulfenyl and the group W is hydrogen, a treatment with a halogenating reagent e.g. iodobenzene dihalide, oxalyl chloride, thionyl halide, phosphorus pentachloride, affords the starting materials for the preceding paragraph (R=sulfinyl).

When the group R is a thio group and W is hydrogen, treatment with an oxidizing reagent e.g. m-chloroperbenzoic acid, perphthalic acid, peracetic acid, iodobenzene dichloride, iodobenzene dichloride-water, in a conventional manner affords the starting material of the preceding paragraph (R=sulfinyl).

When W is hydrogen and R is alkylsulfinyl, the treatment of Compound (27) with a halogenating reagent e.g. thionyl chloride reduces sulfinyl and eliminate hydrogen halide at the same time to obtain carbapenem (28) in one step. This reaction has never appeared in the literature.

Similar introduction of double bond can be found in chemical literature of carbapenem in other fields. The reactions can be also applied to the present purpose. The literature includes J. Chemical Society, Chem. Comm. 1980, 185; Japanese Patent Application Publication (Kokai) 1980-73681; 1979-76593.

5. Migration of a double bond

Treatment of the Compound (2) with a base in an organic or inorganic solvent causes migration of the double bond and the ratio of the position isomers equilibrates after some time.

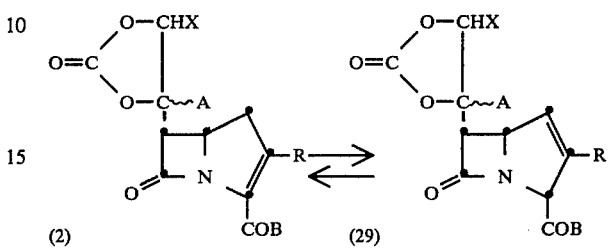

(wherein A, COB, R, X and wave line are as defined above)

The base used here can be DBN, DBU, aromatic base, tertiary amine, secondary amine, or the like. When a strong base e.g. DBN, DBU, is used, the dioxolane ring fission as explained later also take place simultaneously.

The ratio of the position isomers conjugated (2)/non-conjugated (29) changes depending on the conditions e.g. substituents, concentration of reagent, solvent, temperature, and other conditions.

Similar reactions appear in J. Organic Chemistry, 45, 1135, 1142 (1980); Japanese Patent Application Publication 1979-66696. These conditions can also be applied to this reaction.

6. Enolization of β-oxocarboxylate.

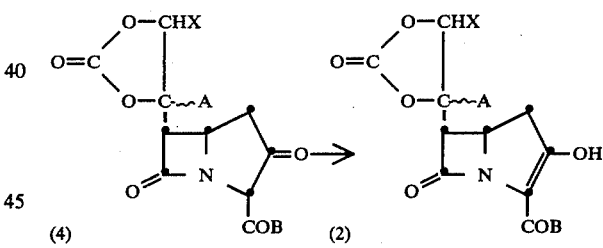

(wherein A, COB, X and wave line are as defined above)

The ketone group in Oxocarboxylate (4) enolizes and when treated with a reactive derivative of sulfonic acid e.g. p-toluenesulfonic acid, p-bromophenylsulfonic acid, p-nitrophenyl sulfonic acid, 2,4,6-triisopropylphenylsulfonic acid, methanesulfonic acid, ethanesulfonic acid or other aromatic or aliphatic sulfonic acid, in a form of acid anhydride or acid halide, affords the corresponding enolsulfonate. This reaction can be carried out in an inert solvent in the presence of an acid scavenger e.g. triethylamine, diisopropylamine, N-methylmorpholine, piperidine, pyridine, picoline, lutidine, or the like aliphatic or aromatic base, at a temperature of $-20°$ C. to 40° C. for 10 minutes to 4 hours. Treatment of the same ketone with a halogenating reagent e.g. phosphorus halide, arylphosphorus halide, phosphorus oxyhalide, diarylchlorophosphate, oxalyl halide, thionyl halide, under similar condition affords the corresponding enol halide.

The produced enol sulfonate or enol halide can be isolated in a manner conventional in the art.

7. Substitution

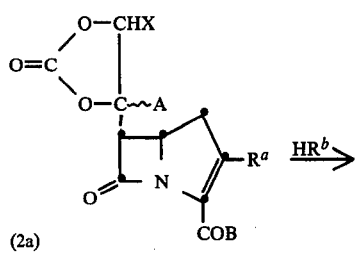

(2a)

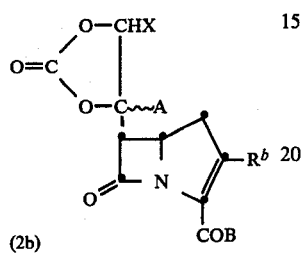

(2b)

(wherein A, COB, X and wave line are as defined above;
$R^a$ is a leaving group; and
$R^b$ is a nucleophilic group)

When $R^a$ group of the compound (2) is a leaving group e.g. halogen, aliphatic or aromatic sulfonyloxy, the compound (2a) can be produced with a nucleophilic reagent having $R^b$ as the nucleophilic group.

The nucleophilic reagents used here include hydrogen azide salts, substituted thiourea, thioamide, aliphatic, aromatic or heterocyclic thiol, dialkylsulfoxide, alcohol, amine, thiocyanic acid, or other compound bearing active hydrogen and the salts thereof.

If required, acid scavenger is added to the reaction mixture to accelerate the reaction. The scavenger includes inorganic bases, aliphatic or aromatic amines, and aromatic bases. The reaction is usually carried out in an inert solvent at $-10°$ C. to $100°$ C. for 30 minutes to 5 hours.

8. Ring fission of dioxolane

2-Azetidinone derivatives (I) having 2-oxo-1,3-dioxolane-4-yl group affords the corresponding allyl alcohol derivatives by the action of inorganic base e.g. sodium hydrogen carbonate, sodium carbonate, potassium carbonate, calcium hydroxide, or or organic base e.g. DBN, DBU, This reaction has never been found in the literature.

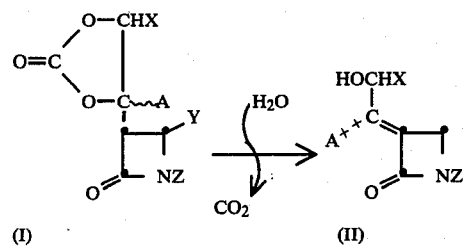

(wherein, A, X, Y, Z, wave line and the line ++++ show the same significances as defined above.)

The reaction is usually carried out at $-10°$ C. to $50°$ C. for 1 minutes to 5 hours when the reagent is DBN or DBU. The reaction is preferably carried out in an industrial solvents e.g. halohydrocarbon e.g. dichloromethane, chloroform, trichloroethane, chlorobenzene, nitrile e.g. acetonitrile, benzonitrile, alcohol e.g. methanol, ethanol, or other aqueous or nonaqueous solvents.

When the reaction is carried out in the presence of silylating reagent e.g. O,N-bistrialkylsilylacetamide to produce allyl alcohol (II) in which the hydroxyl group is silylated. In this case, the silyl group can be eliminated by treating with diluted alcohol at room temperature for 1 to 5 hours or by treating with aqueous acetic acid and tetraethylammonium fluoride in an etheric solvent to afford the desired allyl alcohol. This detour route simplifies the isolation of the products and superior to the direct route.

The alcohol group of hydroxymethyl and carbonyl attached to azetidine ring is in syn position, the 2-hydroxyalkylidene product is unstable, and decomposed by work up. Therefore, mainly anti-geometric isomer can be isolated, in some cases. When the used reaction solvent is non-polar dichloromethane or chloroform the geometric position of hydroxymethyl and lactam carbonyl is different from when the solvent is polar acetonitrile. Utilizing this feature, one can select the solvent to prepare either one of the isomers as main product.

9. Additional explanation.

In handling the reactions as described in the preceding sections No. 1 to 8, one can use if necessary known or conventional procedure or its modification. For example, the described reaction temperature or reaction time must be changed depending on the sort of starting materials or its concentration, and the values are not restrictive in nature. Cited reagents or solvents are a few examples of suitable industrial materials, and it is to be understood naturally an equivalent substance of the same effect are always used instead. The citation is not restrictive.

The product produced in the reaction mixture is usually isolated by concentration, extraction, etc to remove the solvent, and remaining starting materials or by-products are removed by partition, washing, absorption, evaporation, chromatography, precipitation, dilution and the like conventional methods. The obtained product can be purified by recrystallization, reprecipitation, chromatography, lyophilization, or the like methods conventional in the art. The reagents are used 1 equivalent or more, preferably 1 to 5, equivalents, especially 1 to 2 mole equivalents.

The structural formula shows reative steric configuration.

[Examples]

Following examples illustrate some of the embodiments of this invention. The notation to the compound shows numbers of physical constant tables and compound number in the table.

Concentration is usually carried out under reduced pressure until dryness. Drying is made with magnesium sulfate. Silica gel chromatography is carried out with Lobar column distributed by E. Merck A.G. in Darmstadt, West Germany using a mixture of benzene and ethyl acetate and the developing solvent.

(Abbreviations)
Bu=butyl,
Ph=phenyl,
Et=ethyl,
PNB=p-nitro benzyl,
ONB=o-nitrobenzyl,
POM=pivaloyloxymethyl.

Absolute configuration of the 4-carbon on the 2-oxodioxolane ring has not been elucidated. The epimers are identified by tentative naming of a and b series.

On Tables A to M, IR data is shown in cm$^{-1}$ and Ex. No. means Example number in which the compound is described.

EXAMPLE 1.

4-Allyl-3-hydroxyacetyl-1-t-butyldimethylsilyl-2-azetidinone(ii)

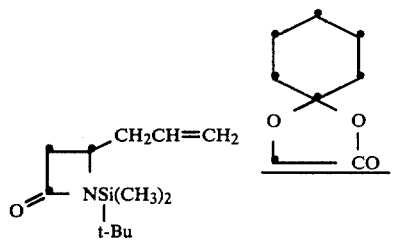

Azetidinone (i)
JCS Chem.Comm.1979,236

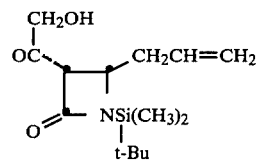

Ketol (ii)

To a solution of diisopropylamine (1.60 g) in tetrahydrofuran (40 ml) cooled at −78° C. under nitrogen is added a solution of n-butyllithium in hexane (1.6N, 15 ml), and the mixture is let warm to 0° C. and stirred for 30 minutes. The solution is cooed again at −78° C. A solution of azetidinone (i) (5.10 g) in tetrahydrofuran (20 ml) is added dropwise to the solution of diisopropyllithiumamide as prepared above, and the mixture is stirred for 30 minutes. To the reaction mixture containing 3-lithio derivative of Azetidinone (i) is added a solution of 1,4-dioxaspiro[5,4]decan-2-one (3.75 g), in tetrahydrofuran (10 ml) dropwise and the mixture is stirred at the same temperature for 1 hour. The reaction mixture is acidified with acetic acid (1.80 g), poured onto saline, and extracted with ethyl acetate. The extract is dried and concentrated. The residue is treated by silica gel chromatography to give the starting azetidinone (i) (2.0 g) and ketol (ii) (3.0 g).

Ketol (ii):

IR: $\nu_{max}^{CHCl_3}$ 1715, 1740 cm$^{-1}$.

NMR: $\delta_{ppm}^{CDCl_3}$ 0.23(s, 3H), 0.30(s, 3H), 1.00(s, 9H), 2.1–2.9(br m, 2H), 3.5–3.8(br,1H), 4.0–4.5(m, 4H), 4.95–6.2(m, 3H).

EXAMPLE 2

4-Allyl-1-dimethyl-t-butylsilyl-3-(1,2-dihydroxy-2-propyl)-2-azetidinone (A-3,4)

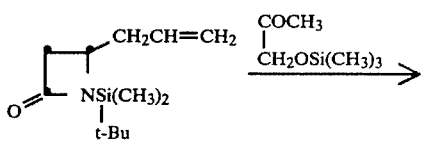

Azetidinone (i)

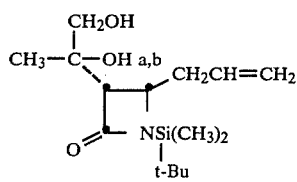

Diol (A-3,4)

In tetrahydroufran (50 ml), lithium diisopropylamide is prepared from diisopropylamine (3.2 g) and a solution of 1.6N-n-butyllithium in hexane (20 ml). This solution is cooled at −78° C., mixed with a solution of Azetidinone (i) (4.5 g) in tetrahydrofuran (10 ml) and stirred under nitrogen for 40 minutes. To the mixture is added hydroxyacetone trimethylsilyl ether (7.5 ml) and the mixture is stirred for 30 minutes. Ethyl acetate and saline are added to the reaction mixture, and organic layer is separated. This is dried and concentrated. The residue is dissolved in methanol (30 ml), acidified with acetic acid (3 ml) and kept overnight at room temperature. The solution is concentrated and the residue obtained is purified by silica gel chromatography to give the tilted diol from the fractions eluted with benzene-ethyl acetate (1:1) mixture. Thus, the stereoisomers (A-3)(3.02 g) and (A-4)(1.30 g) due to α-position of side chain on the 3 position are obtained.

EXAMPLE 3

4-Allyl-1-t-butyldimethylsilyl-3-(1,2-dihydroxyethyl)-2-azetidinone (A-1,2)

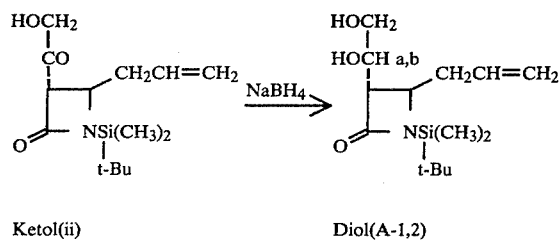

Ketol(ii)                              Diol(A-1,2)

To a solution of Ketol (ii) (3.1 g) in methanol (30 ml) is added sodium borohydride (250 mg) at −78° C., and the mixture is stirred at the same temperature for 1 hour. The reaction mixture is diluted with ethyl acetate, washed with saline, dried and concentrated. The residue is chromatographed over silica gel to give the stereoisomers of Diol (A) i.e. A-1 (1.92 g) from faster fractions and A-2 (0.76 g) from slower fractions.

EXAMPLE 4

4-Allyl-1-t-butyldimethylsilyl-3-(2-oxo-1,3-dioxolan-4-yl)-2-azetidinone (B-1,2)

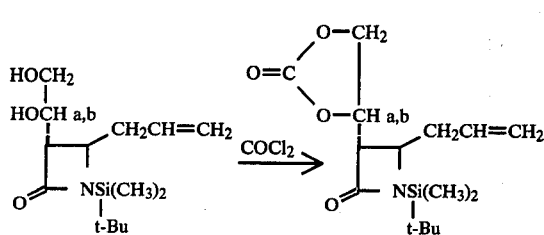

Diol(A-1,2)    Dioxolane(B-1,2)

To a solution of Diol (A-1)(1.92 g) and pyridine (1.5 ml) in dichloromethane (20 ml) is added a solution of phosgene in toluene (2.6N, 3.0 ml) cooled at −20° C., and then the mixture is warmed to 0° C. and stirred for 1 hour. The reaction mixture is diluted with ethyl acetate, washed with water, dried and concentrated to give dioxolane (B-1)(2.1 g).

Under the same condition, Diol (A-2)(0.76 g) is cyclized with phosgene to give dioxolane (B-2)(0.80 g).

EXAMPLE 5

4-Allyl-1-t-butyldimethylsilyl-3-(4-methyl-2-oxo-1,3-dioxolan-4-yl)-2-azetidinone (B-3,4)

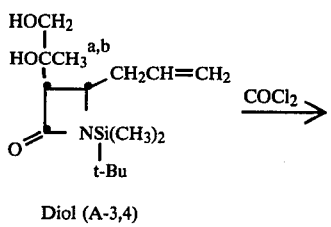

Diol (A-3,4)

Dioxolane (B-3,4)

To a solution of Diol (A-3) (3.02 g) in a mixture of dichloromethne (20 ml) and pyridine (1.60 g) is added a solution of phosgene in toluene (3M, 3.6 ml) under ice cooling, and the mixture is stirred for 30 minutes. The reaction mixture is diluted with ethyl acetate, washed with water, dried and concentrated to give Dioxolane (B-3)(3.10 g).

Under the same condition Diol (A-4)(1.30 g) gives Dioxolane (B-4)(1.54 g) with phosgene.

EXAMPLE 6

4-Allyl-3-(2-oxo-1,3-dioxolan-4-yl)-2-azetidinone (C-1,2)

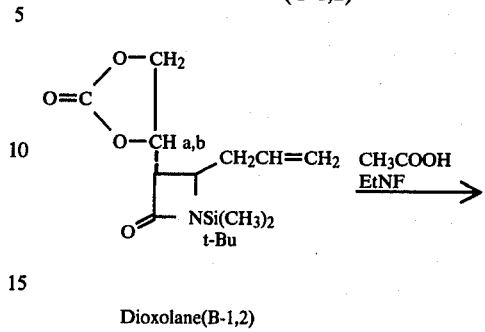

Dioxolane(B-1,2)

Lactam(C-1,2)

To a solution of Dioxolane (B-1)(2.1 g) and acetic acid (1.0 ml) in tetrahydrofuran (20 ml) is added tetraethylammonium dihydrate (1.5 g), and the mixture is stirred at room temperature for 1 hour. The reaction mixture is diluted with dichloromethane washed with saline, dried and concentrated. The residue is purified by silica gel chromatography to give Lactam (C-1)(1.26 g).

Under the same condition, Dioxolane (B-2)(0.69 g) gives Lactam(C-2)(0.49 g).

EXAMPLE 7

4-Allyl-3-(4-methyl-2-oxo-1,3-dioxolan-4-yl)-2-azetidinone (C-3,4)

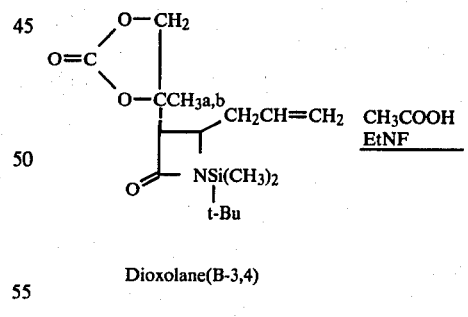

Dioxolane(B-3,4)

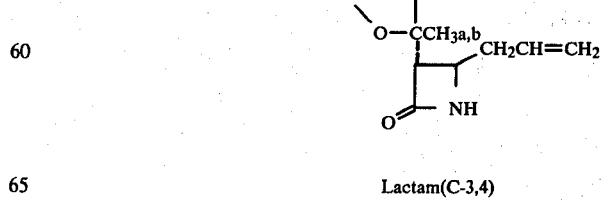

Lactam(C-3,4)

To a solution of dioxolane (B-3)(4.50 g) in tetrahydrofuran are added acetic acid (1.6 ml) and tetraethylammonium fluoride dihydrate (2.5 g), and the mixture is stirred at room temperature for 1 hour. The reaction mixture is diluted with ethyl acetate, washed with saline, dried and concentrated. The residue is chromatographed over silica gel to give Lactam(C-3)(2.81 g).

Under the same condition, Dioxolane (B-4)(1.33 g) gives Lactam (C-4)(0.90 g).

EXAMPLE 8

3-(4-Methyl-2-oxo-1,3-dioxolan-4-yl)-4-(2-oxopropyl)-2-azetidinone (C-5)

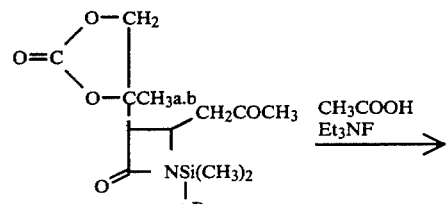

Dioxolane(B-5)

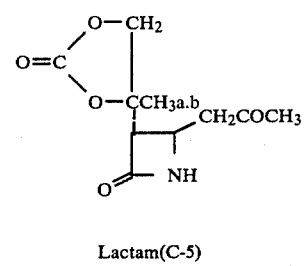

Lactam(C-5)

A mixture of Dioxolane (B-5)(1.62 g), tetraethylammonium fluoride dihydrate (1.38 g) and acetic acid (0.5 ml) in tetrahydrofuran (10 ml) is stirred at room temperature for 2 hours. The reaction mixture is diluted with ethyl acetate (50 ml), washed with saturated saline, dried and concentrated. The residue purified by silica gel chromatography to give tilted Lactam (C-5)(895 mg) from the fractions eluted with benzene-ethyl acetate (1:5).

EXAMPLE 9

3-(4-Methyl-2-oxo-1,3-dioxolan-4-yl)-4-(2-oxopropyl)-2-azetidinone (C-6)

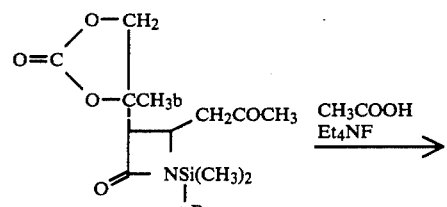

Dioxolane(B-6)

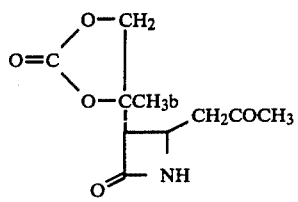

Lactam(C-6)

A solution of Acetonylester (B-6)(1.2 g), tetraethylammonium fluoride dihydrate (3 g) and acetic acid (0.4 g) in tetrahydrofuran (10 ml) is stirred at room temperature for 2 hours. The reaction mixture is diluted with ethyl acetate (50 ml), washed with saturated saline, dried and concentrated. Purification of the residue by silica gel chromatography gives the tilted Lactam(C-6)(535 mg) from the fractions eluted with a mixture of ethyl acetate and benzene (5:1)

EXAMPLE 10

α-[4-Allyl-3-(4-methyl-2-oxo-1,3-dioxolan-4-yl)-2-azetidinon-1-yl]glycolic acid (D-10, 11)

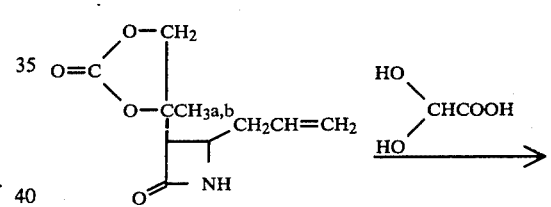

Lactam(C-3,4)

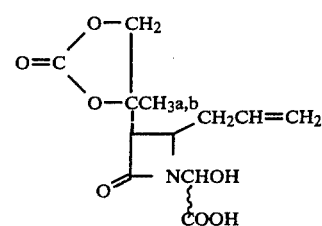

Glycolic acid(D-10,11)

A solution of Lactam (C-3)(211 mg) and glyoxylic acid hydrate (160 mg) in dimethylformamide (1 ml) is mixed with Molecular Sieves 4 A (0.6 g) and kept at room temperature for overnight. The reaction mixture is diluted with ethyl acetate, washed with saturated saline, dried and concentrated to give glycolic acid (D-10)(330 mg).

Under the same condition, Lactam (C-4) (363 mg) gives Glycolic acid (D-11) (610 mg).

EXAMPLE 11

α-[4-allyl-3-(4-methyl-2-oxo-1,3-dioxolan-4-yl)-2-azetidinon-1-yl]glycolic acid o-nitrobenzyl ester (D-5)

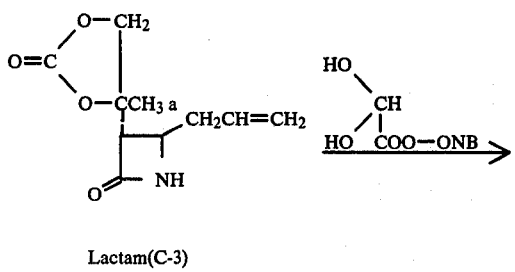

Lactam(C-3)

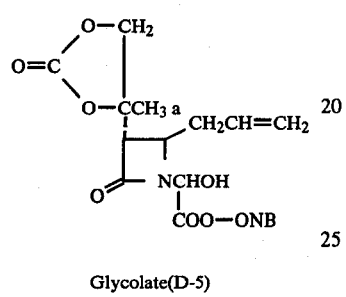

Glycolate(D-5)

A mixture of Lactam (C-3)(0.75 g), glyoxylic acid o-nitrobenzyl ester (0.78 g) and triethylamine 20 μl in tetrahydrofuran (10 ml) is kept at room temperature for 2 days, and concentrated. The residue is dissolved in ethyl acetate, washed with aqueous sodium sulfite and saline, dried and concentrated to give the captioned glycolate (D-5)(1.80 g).

EXAMPLE 12

α-[4-Allyl-3-(2-oxo-1,3-dioxolan-4-yl)-2-azetidinon-1-yl]-α-triphenylphosphoranilideneacetic acid p-nitribenzyl ester(E-1, 2)

A mixture of lactam (C-1)(260 mg), glyoxylic acid p-nitrobenzyl ester (300 mg), triethylamine (20 μl) and tetrahydrofuran (4 ml) is kept at room temperature overnight. The reaction mixture is concentrated to give glycolate (D-1). This is dissolved in tetrahydrofuran (10 ml), cooled to −40° C. under nitrogen, mixed with 2,6-lutidine (0.30 ml) and thionyl chloride (0.15 ml), and stirred at −30° C. to −20° C. for 1 hour. The solution is concentrated the corresponding chloroacetate. This is dissolved in dioxane (4 ml), 2,6-lutidine (0.2 ml), and triphenylphosphine (0.40 g) are added thereto, and the mixture is stirred at room temperature overnight. The solution is diluted with ethyl acetate, washed with water, dried and evaporated. The residue is purified by silica gel chromatography to give the phosphorane (E-1)(589 mg).

Under the same condition, phosphorane (E-2)(490 mg) is prepared from lactam (C-2)(233 mg) through the corresponding glycolate and chloroacetate.

EXAMPLE 13

α-[3-(4-Methyl-2-oxo-1,3-dioxolan-4-yl)-4-(2-oxopropyl)-2-azetidinon-1-yl]-α-triphenylphosphoranylideneacetic acid p-nitrobenzyl ester(E-9,10)

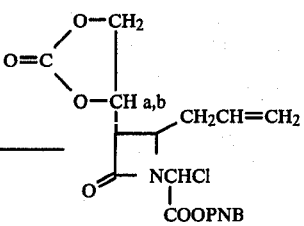

Lactam(C-5,6)

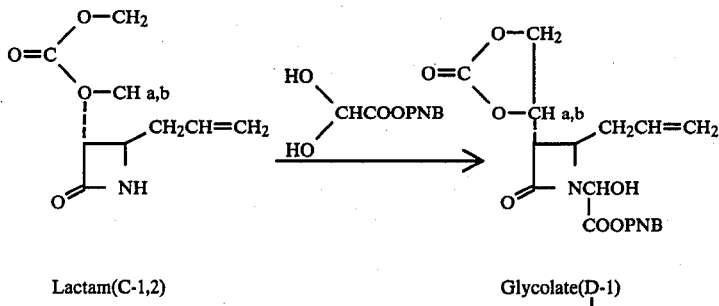

Lactam(C-1,2)    Glycolate(D-1)

Phosphorane(E-1,2)    Chloroacetate

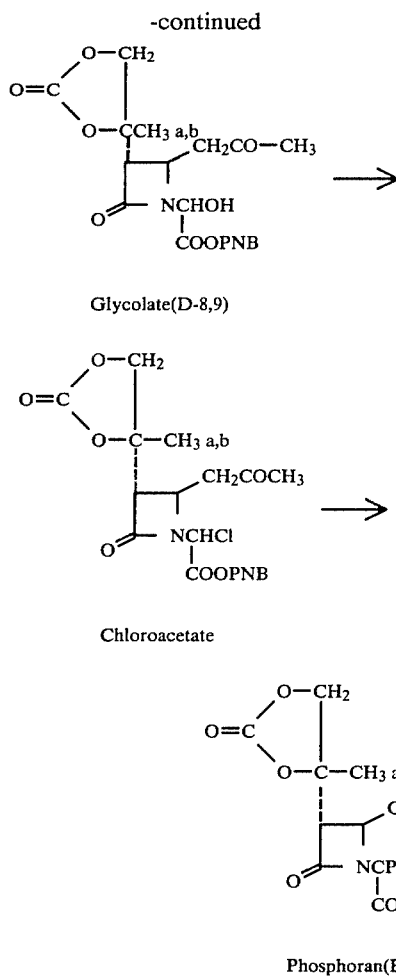

Glycolate(D-8,9)

Chloroacetate

Phosphoran(E-9,10)

(1) A mixed solution of Lactam (C-5)(795 mg), triethylamine (20 µl) and glyoxylic acid p-nitrobenzyl ester monohydrate (954 mg) in tetrahydrofuran (10 ml) is stirred with Molecular Sieves 4 A at room temperature for 3 hours. The reaction mixture is concentrated. The residue is dissolved in ethyl acetate (20 ml), washed with saturated saline, dried and evaporated to give Glycolate (D-8)(1.45 g).

This is dissolved in tetrahydrofuran (20 ml). Thionyl chloride (475 µl) and 2,6-lutidine (759 µl) are added to the solution and the mixture is stirred at −20° C. for 2 hours and at 0° C. for 30 minutes. The reaction mixture is filtered to remove solid and concentrated to give the corresponding chloroacetate.

IR: $\nu_{max}^{CHCl_3}$ 1805, 1780, 1151 cm$^{-1}$.

The obtained chloroacetate, triphenylphosphine (1.73 g) and 2,6-lutidine (1.8 ml) are dissolved in dioxane (5 ml), and the mixture is stirred at room temperature for 14 hours in the presence of Molecular Sieves 4 A. The mixture is then filtered, and concentrated. The residue is purified by silica gel chromatography to give the captioned phosphorane (E-9)(1.15 g) from the fractions eluted with ethyl acetate.

(2) Under the same condition, Lactam (C-6) (476 mg) gives Phosphorane (E-10)(590 mg) through the corresponding Glycolate (D-9)(789 mg).

EXAMPLE 14

α-[4-Allyl-3-(4-methyl-2-oxo-1,3-dioxolan-4-yl)-2-azetidinon-1-yl]-α-triphenylphosphoranylideneacetic acid p-nitrobenzyl ester (E-7,8)

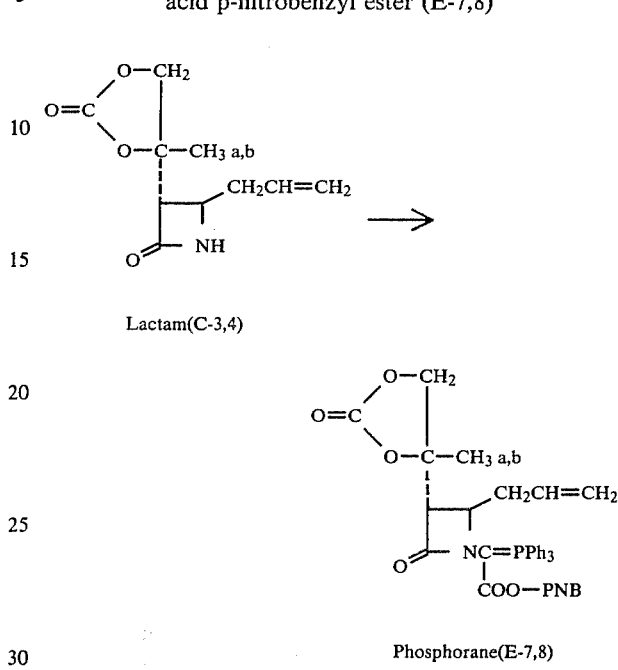

Lactam(C-3,4)

Phosphorane(E-7,8)

A mixed solution of Lactam (C-3)(1.79 g), glyoxylic acid p-nitrobenzyl ester (1.93 g), triethylamine (40 µl) and tetrahydrofuran (30 ml) is kept at room temperature overnight and then concentrated. The residual Glycolate (D-6,7) is dissolved in tetrahydrofuran (25 ml), cooled to −35° C., mixed with 2,6-lutidine (1.73 g) and thionyl chloride (1.45 g), kept at −35° C. to −20° C. for 1.5 hours with stirring, and then concentrated in vacuo to remove the solvent and reagent. The residue is mixed with dioxane (25 ml), 2,6-lutidine (1.0 ml), and triphenylphosphine (3.0 g), and the mixture is stirred at room temperature overnight. The reaction mixture is diluted with ethyl acetate, washed with water, dried and concentrated. The residue is purified by silica gel chromatography to give the captioned Phosphorane (E-7)(4.42 g).

Under the same condition, Lactam (C-4) (0.75 g) gives the Phosphorane (E-8)(4.42 g).

EXAMPLE 15

α-[4-Allyl-3-(2-oxo-1,3-dioxolan-4-yl)-2-azetidinon-1-yl]-α-triphenylphosphoranilideneacetic acid pivaloyloxymethyl ester (E-3)

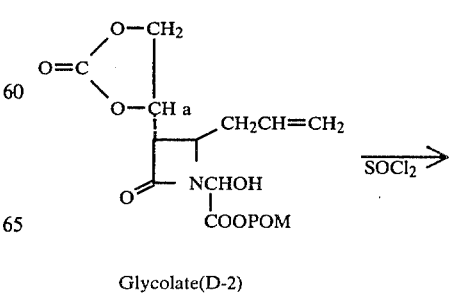

Glycolate(D-2)

-continued

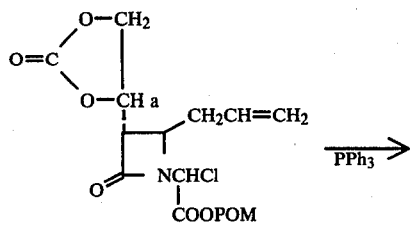

Chloroacetate

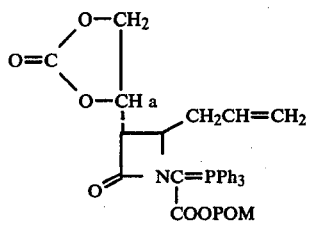

Phosphorane(E-3)

A solution of Glycolate (D-2)(536 mg), pyridine (144 μl) and thionyl chloride (110 μl) in dichloromethane (15 ml) at −25° C. is stirred at the same temperature for 20 minutes. The reaction mixture is washed with water, dried and concentrated to give the corresponding Chloroacetate (508 mg). This is dissolved in dioxane (5 ml), mixed with triphenylphosphine (0.52 g) and vinylpyridine-styrene copolymer (1.5 g), and kept at room temperature overnight. After the solid is filtered off, the reaction mixture is; concentrated, the residue is purified by silicagel chromatography to give the captioned Phosphorane (E-3)(611 mg).

EXAMPLE 16

α-[4-Allyl-3-(4-methyl-2-oxo-1,3-dioxolan-4-yl)-2-azetidinon-1-yl]-α-triphenylphosphoranilideneacetic acid pivaloyloxymethyl ester (E-4,5)

-continued

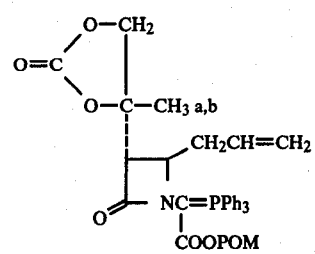

Phosphorane(E-4,5)

To a solution of Glycolate (D-3)(370 mg) in tetrahydrofuran (2 ml) cooled at −30° C. under nitrogen are added 2,6-lutidine (215 mg) and thionyl chloride (240 mg), and the mixture is stirred for 30 minutes. The reaction mixture is diluted with tetrahydrofuran, filtered to remove solid and concentrated to give the corresponding Chloroacetate.

The chloroacetate is dissolved in a mixture of dioxane (2 ml) and 2,4-lutidine (150 μl), mixed with triphenylphosphine (0.45 g), and the mixture is stirred at room temperature for 4 hours under nitrogen. The reaction mixture is diluted with ethyl acetate, washed with water, dried and concentrated. The residue is purified by silica gel chromatography to give Phosphorane (E-4)(428 mg) from the fractions eluted with a mixture of benzene and ethyl acetate (2;1).

Under the same condition, GlycolAte (D-4)(540 mg) gives the corresponding Phosphorane (E-5)(476 mg) through Chloroacetate.

EXAMPLE 17

α-[4-Allyl-3-(4-methyl-2-oxo-1,3-dioxolan-4-yl)-2-azetidinon-1-yl]-α-triphenylphosphoranilideneacetic acid o-nitrobenzyl ester (E-6)

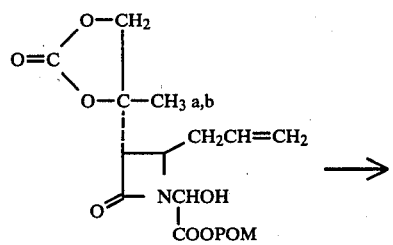

Glycolate(D-3,4)

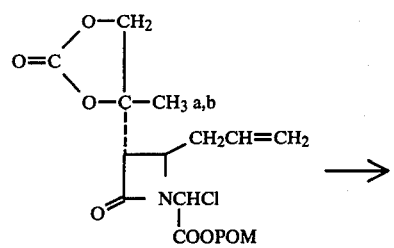

Chloroacetate

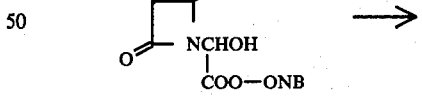

Glycolate(D-5)

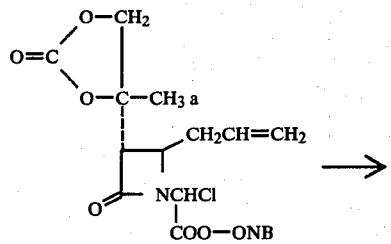

Chloroacetate

-continued

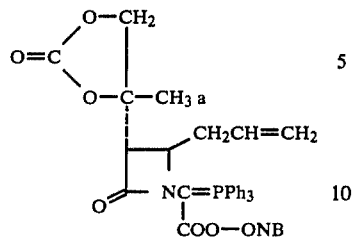

Phosphorane(E-6)

To a solution of glycolate (D-5)(1.80 g) in tetrahydrofuran (10 ml) cooled at −30° C. under nitrogen are added 2,6-lutidine (0.76 g) and thionyl chloride (0.86 g), and the mixture is stirred for 30 minutes at −30° C. to −20° C. The reaction mixture is filtered to remove solid, which is washed with tetrahydrofuran, and filtrate and washings are combined to concentrate to yield the corresponding Chloroacetate. This is dissolved in dioxane (10 ml). 2,6-Lutidine (0.60 g) and triphenylphosphine (1.2 g) are added to the mixture. After stirring overnight at room temperature, the mixture is diluted with ethyl acetate, filtered to collect solid. This is dissolved in dichloromethane, washed with water, dried and concentrated to leave crystalline residue the captioned Phosphorane (E-6)(230 mg).

EXAMPLE 18

6-(2-oxo-1,3-dioxolan-4-yl)-7-oxo-1-azabicyclo[3.2.0-]hept-2-en-2-carboxylic acid p-nitrobenzyl ester (F-1,2)

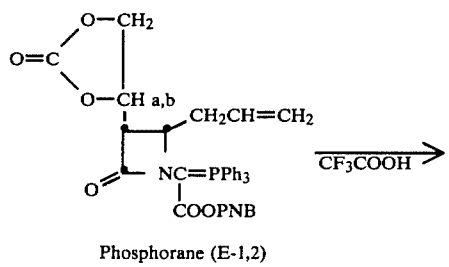

Phosphorane (E-1,2)

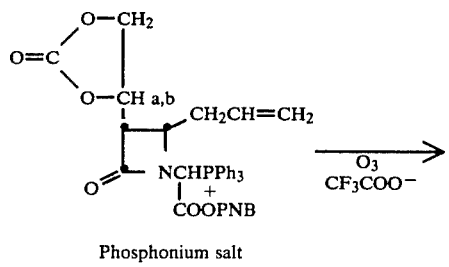

Phosphonium salt

-continued

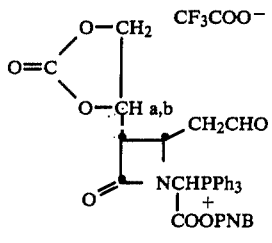

Aldehyde

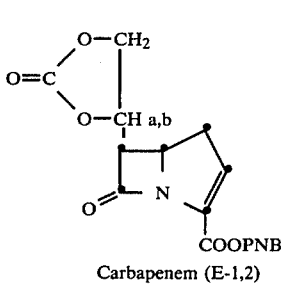

Carbapenem (E-1,2)

To a solution of the phosphorane (E-1)(589 mg) in dichloromethane (10 ml) is added trifluoroacetic acid (0.50 ml) at −78° C. to obtain a solution of Phosphonium salt. To this solution is passed into ozone until blue color appears. Then, nitrogen is passed the solution to purge excess ozone. Dimethyl sulfide (0.5 ml) is added to the solution and allowed to react at room temperature for 30 minutes. The reaction mixture is concentrated to dryness. This is dissolved in ethyl acetate (20 ml) and stirred at room temperature in the presence of aqueous saturated sodium hydrogen carbonate. After 1 hour's stirring, separated crystals are collected by filtration, washed with water and ethyl acetate, and dried to give Carbapenem (F-1)(200 mg). mp. 172°–174° C.

Under the same condition, Phosphorane (E-2)(490 mg) gives Carbapenem (F-2)(146 mg) through the corresponding Phosphonium salt and Aldehyde. mp. 144°–145° C. (Carbapenem).

EXAMPLE 19

6-(2-Oxo-1,3-dioxolan-4-yl)-7-oxo-1-azabicyclo[3.2.0]-2-heptene-2-carboxylic acid pivaloyloxymethyl ester (F-3)

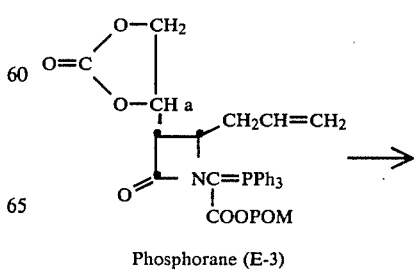

Phosphorane (E-3)

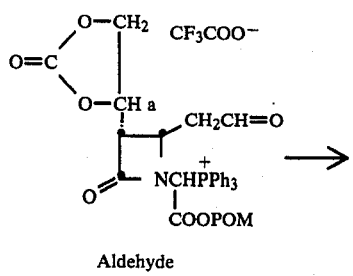

Aldehyde

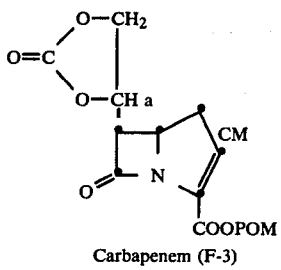

Carbapenem (F-3)

To a solution of Phosphorane (E-3)(0.6 g) in dichloromethane (30 ml) is added trifluoroacetic acid (1 ml) and passed ozone at −65° C. Then, nitrogen is passed through the solution. Dimethyl sulfide (2 ml) is added and allowed to react to 0° C. for 10 minutes with stirring. The reaction mixture is treated with aqueous 7% sodium hydrogen carbonate, washed three times with water, and evaporated. The residue is crystallized from ethyl acetate-dichloromethane mixture to give the captioned Carbapenem (F-3)(161 mg). mp. 175°–177° C.

EXAMPLE 20

6-(4-Methyl-2-oxo-1,3-dioxolan-4-yl)-7-oxo-1-azabicyclo[3.2.0]-hept-2-en-2-carboxylic acid pivaloyloxymethyl ester (F-4,5)

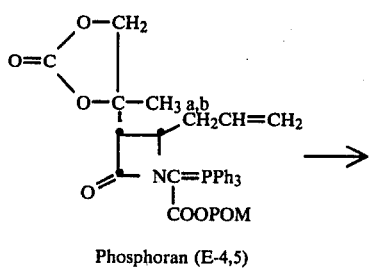

Phosphoran (E-4,5)

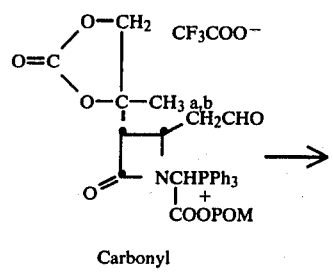

Carbonyl

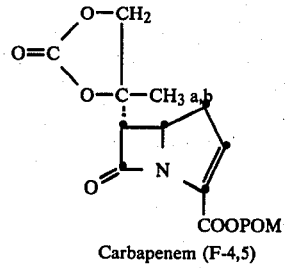

Carbapenem (F-4,5)

To a solution of Phosphoran(E-4) (428 mg) in dichloromethane (15 ml) cooled at −78° C. is added trifluoroacetic acid (1 ml). To the mixture is added ozone until blue color appears. Dimethylsulfide (8 ml) is added to the solution and warmed to room temperature. After 1 hour's stirring, the reaction mixture is concentrated. The residue is dissolved in ethyl acetate (10 ml), aqueous saturated sodium hydrogen carbonate (10 ml) is added thereto and allowed to react at room temperature for 2 hours with vigorous stirring. Organic layer is separated, dried and concentrated. The residue is purified by silica gel chromatography to give Carbapenem (F-4) (150 mg).

Under the same condition, Phosphorane (E-5) (476 mg) gives Carbapenem(F-5) (160 mg) through the corresponding Carbonyl.

EXAMPLE 21

6-(4-Methyl-2-oxo-1,3-dioxolan-4-yl)-7-oxo-1-azabicyclo[3.2.0]-2-hepten-2-carboxylic acid p-nitrobenzyl ester (F-6,7)

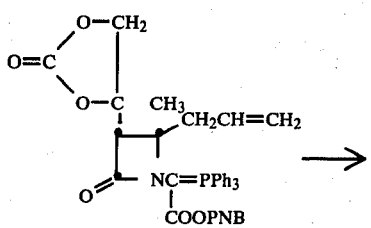

Phosphorane (E-7,8)

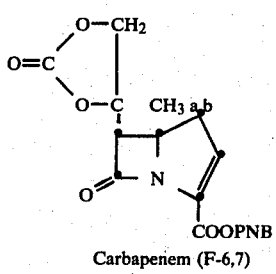

Carbapenem (F-6,7)

(1) To a solution of Phosphorane (E-7) (1.10 g) in dichloromethane (30 ml) cooled at −60° C. is added trifluoroacetic acid (2 ml), is passed ozone and then bubbled nitrogen. The mixture is mixed with dimethyl sulfide (2 ml), stirred at room temperature for 1 hour, and concentrated. The residue is dissolved in ethyl acetate (20 ml), washed with aqueous saturated sodium hydrogen carbonate (20 ml) and stirred for 1 hour at room temperature. Organic layer is separated, washed with water, dried and concentrated. The residue is crystallized from a mixture of ether and benzene to give the captioned Carbapenem (F-6) (0.35 g).

(2) Under the same condition, Phosphoran (E-8) (1.23 g) gives the captioned Carbapenem (F-7) (317 mg).

EXAMPLE 22

6-(4-Methyl-2-oxo-1,3-dioxolan-4-yl)-7-oxo-1-azabicyclo[3.2.0]-hept-2-en-2-carboxylic acid o-nitrobenzyl ester (F-8)

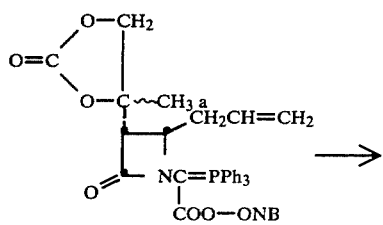

Phosphorane (E-6)

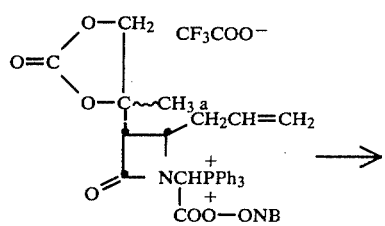

Phosphonium salt

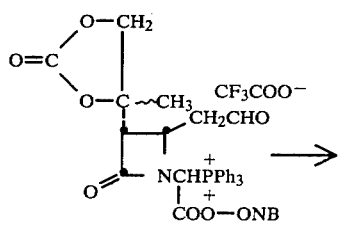

Aldehyde

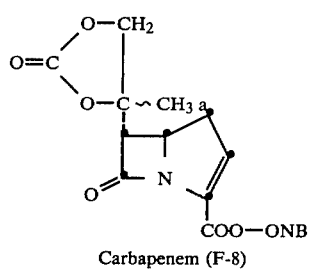

Carbapenem (F-8)

To a solution of Phosphorane (E-6) (2.30 g) in dichloromethane (35 ml) cooled at −50° C. are added trifluoroacetic acid (2 ml) to give Phosphonium salt and ozone until blue color appears. Excess ozone is purged with nitrogen. After dimethyl sulfide (2.5 ml) is added, the mixture is stirred for 1 hour at room temperature. The mixture is concentrated to give Aldehyde. This is dissolved in ethyl acetate (20 ml) and then stirred with aqueous saturated sodium hydrogen carbonate (20 ml) to separate precipitation. After standing overnight, the reaction mixture is filtered to collect the solid. This is washed with water and ethyl acetate to give the captioned Carbapenem (F-8) (800 mg).

EXAMPLE 23

3-Acetamidovinylthio-6-(4-methyl-2-oxo-1,3-dioxolan-4-yl)-7-oxo-1-azabicyclo[3.2.0]hept-2-en-2-carboxylic acid p-nitrobenzyl ester (F-14)

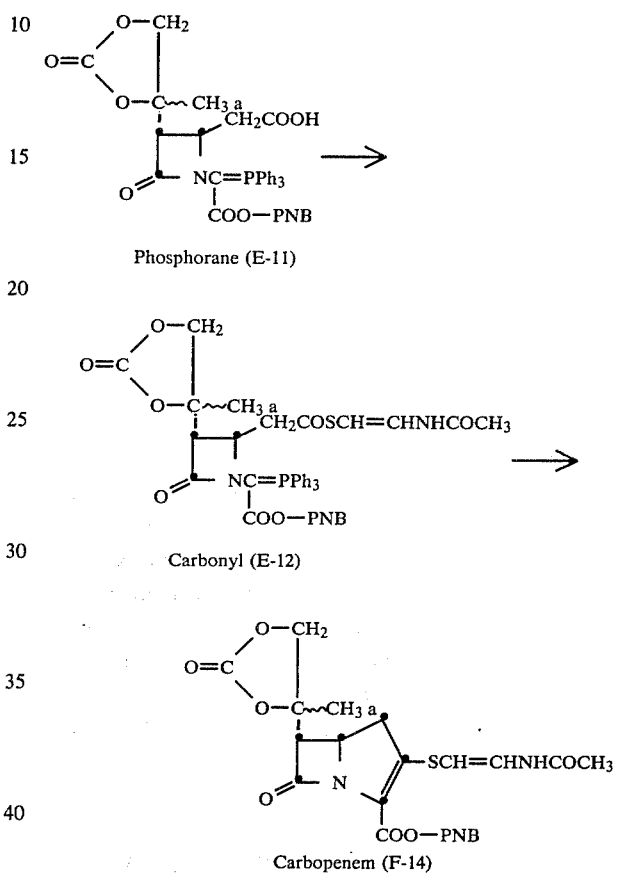

To a solution of Phosphoran (E-11) (2.16 g) and dimethylformamide (10drops) in acetronitrile is added thionyl chloride (0.24 ml), and the mixture is stirred at room temperature for 4 hours. The reaction mixture is mixed with pyridine (0.31 ml) and silver 2-acetamidoethenylthiolate (1.1 g) and stirred at at 0° C. for 2 hours. The reaction mixture is filtered through a column of Hyflo Super Cel and then chromatographed over silica gel to give the captioned Carbonyl (E-12) (0.5 g) from the fractions eluted with ethyl acetate containing 5 to 10% ethanol.

This is refluxed for 30 hours in toluene (150 ml). The reaction mixture is evaporated and the residue is purified with silica gel to give the carbonyl compound (E-12) (422 mg) and the captioned Carbapenem (F-14) (9 mg). Repeated refluxing of recovered Carbonyl (E-12) further gave the same Carbapenem (F-14) compound (53 mg).

EXAMPLE 24

3-Methyl-6-(4-methyl-2-oxo-1,3-dioxolan-4-yl)-7-oxo-1-azabicyclo[3.2.0]hept-2-en-2-carboxylic acid p-nitrobenzyl ester (F-9, 10)

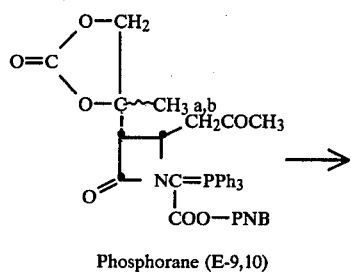

Phosphorane (E-9,10)

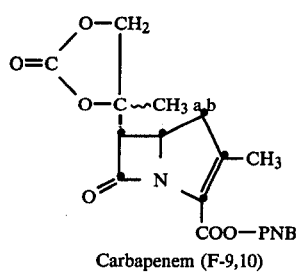

Carbapenem (F-9,10)

(1) Phosphorane (E-9) (1.15 g) is dissolved in toluene (50 ml) and refluxed for 15 hours under nitrogen. Reaction mixture is concentrated, obtained residue is purified by chromatography to give the captioned Carbapenem (F-9) (435 mg) from the fractions eluted with ethyl acetate-benzene (3:1) mixture.

(2) Under the same condition, Phosphorane (E-10) (590 mg) gives Carbapenem (F-10) (180 mg).

EXAMPLE 25

4-Carboxymethyl-1-t-butyldimethylsilyl-3-(4-methyl-2-oxo-1,3-dioxolan-4-yl)-2-azetidinone (B-7)

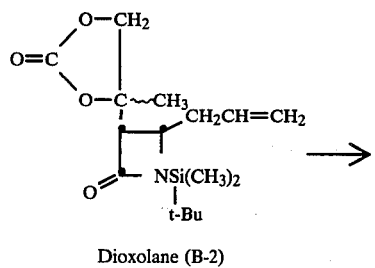

Dioxolane (B-2)

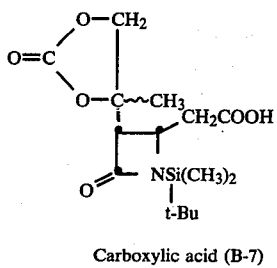

Carboxylic acid (B-7)

To a solution of Dioxolane of Example 4 (B-2) (2.4 g) in dichloromethane (100 ml) cooled at −70° C. is introduced ozone until blue color appears. Then nitrogen is passed to the solution to purge excess ozone. Dimethyl sulfide (6.6 ml) is added to the mixture. After 1 hour stirring at room temperature, the reaction mixture is washed with water, dried and concentrated. The residue is dissolved in acetone (30 ml), oxidized with a small excess of Jones' reagent, stirred for 10 minutes and mixed with methanol. After 20 minutes stirring, the mixture is diluted with ethyl acetate (200 ml), passed through Hyflo Super Cel layer and concentrated. The residue is washed with aqueous 5% sodium hydrogen carbonate to extract acid substance. The obtained washing is washed with dichloromethane twice, acidified with hydrochloric acid, and extracted with ethyl acetate. The extract is washed with saturated saline, dried and concentrated to dryness. The residue is triturated in ether to give the captioned Carboxylic acid (B-7) (0.92 g).

EXAMPLE 26

3-(4-Methyl-2-oxo-1,3-dioxolan-4-yl)-4-p-nitrobenzyloxycarbonyl-acetylmethyl-2-azetidinone (C-7)

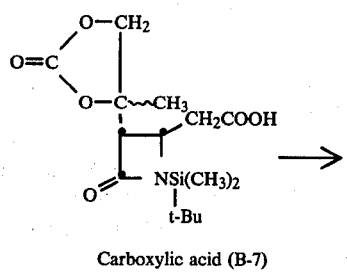

Carboxylic acid (B-7)

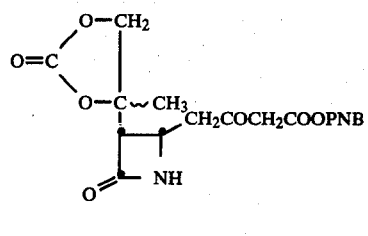

Ketoester (C-7)

To a solution of Carboxylic acid (B-7) (0.92 g) in tetrahydrofuran (15 ml) is added N,N'-carbonyldiimidazole (480 mg), and the mixture is stirred at room temperature for 6 hours. To this solution is added malonic acid mono-p-nitrobenzyl ester monomagnesium salt (1.5 equivalent) in tetrahydrofuran (15 ml). After 7 hours stirring at room temperature, the mixture is diluted with ethyl acetate (200 ml), washed with water, dried and evaporated. The residue (0.9 g) is dissolved in tetrahydrofuran (5 ml), cooled at 0° C. and mixed with acetic acid (0.1 ml) and tetraethylammonium dihydrate (321 mg). After 5 minutes, the mixture is diluted with ethyl acetate (50 ml), washed with water, dried and concentrated. The residue is purified by silica gel chromatography to give the captioned Ketoester (C-7) (230 mg).

EXAMPLE 27

3-(4-Methyl-2-oxo-1,3-dioxolan-4-yl)-4-p-nitrobenzyloxycarbonyldiazoacetylmethyl-2-azetidinone (C-8)

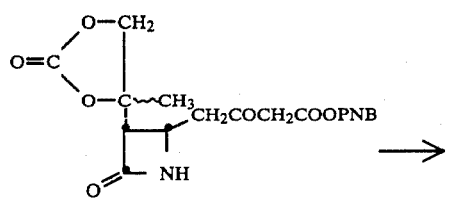

Ketoester (C-7)

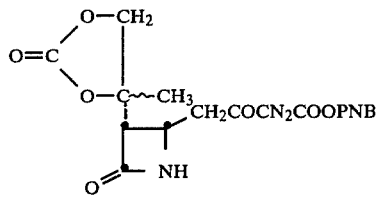

Diazoketone (C-8)

To a solution of Ketoester (C-7) (290 mg) in acetonitrile (36 ml) are added triethylamine (149 μl) and p-toluenesulfonyl azide (211 mg), and the mixture is stirred for 30 minutes under ice cooling. The reaction mixture is diluted with ethyl acetate (100 ml), washed with water, dried and concentrated. The residue is purified by silica gel chromatography to give the captioned diazoketone (C-8) (279 mg).

EXAMPLE 28

6α-(4-Methyl-2-oxo-1,3-dioxolan-4-yl)-3,7-dioxo-1-azabicyclo-[3.2.0]heptan-2α-carboxylic acid p-nitrobenzyl ester (F-9).

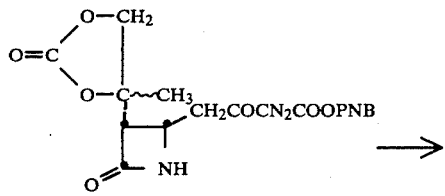

Diazoketone (C-8)

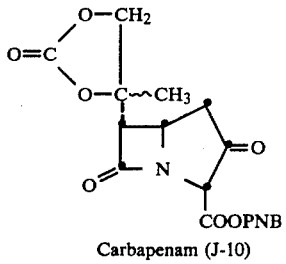

Carbapenam (J-10)

To a suspension of Diazoketone (C-8) (258 mg) in benzene (30 ml) is added rhodium acetate (catalytic amount), and the mixture is stirred for 30 minutes at 75° C. The reaction mixture is concentrated and the residue is purified by silica gel Chromatography to give the captioned Carbapenam (J-10) (211 mg).

EXAMPLE 29

α-[3-(4-Methyl-2-oxo-1,3-dioxolan-4-yl)-4-carboxymethyl-2-azetidinon-1-yl]-α-triphenylphosphoranilideneacetic acid p-nitrobenzyl ester (E-11)

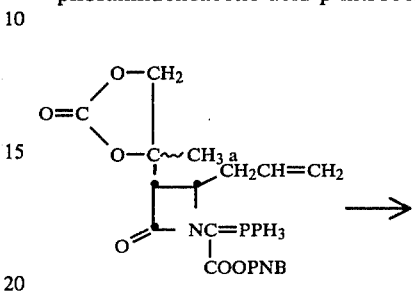

Phosphorane (E-7)

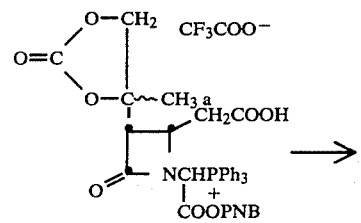

Phosphonium salt (E-13)

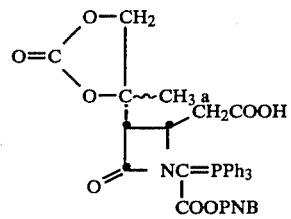

Phosphoranecarboxylic acid (E-11)

To a solution of Phosphorane (E-7) (3.33 g) in dichloromethane (125 ml) is added trifluoroacetic acid (3.5 ml), and the mixture is cooled to −40° C. to −50° C. and bubbled with ozone until blue color appears in the solution. After 5 minutes, excess ozone is purged with bubbling nitrogen in the solution, and the reaction mixture is oxidized with a solution of m-chloroperbenzoic acid (1 g) in dichloromethane (20 ml). After the mixture is allowed to warm to room temperature slowly, it is allowed to stand overnight. The mixture is concentrated, the residue is triturated in ether (100 ml) to form Phosphoniumcarboxylic acid trifluoroacetic acid salt (E-13) (3.59g) as crystals. These are collected by filtration, dissolved in ethyl acetate (100 ml), stirred with neutral alumina (5 g) and filtered. The filtrate is concentrated to give the captioned Phosphoranecarboxylic acid (E-11) (2.35 g).

EXAMPLE 30

1-t-Butyldimethylsilyl-3-(4-methyl-2-oxo-1,3-dioxolan-4-yl)-2-oxo-1,3-dioxolan-4-(2-oxopropyl)-2-azetidinone (B-5)

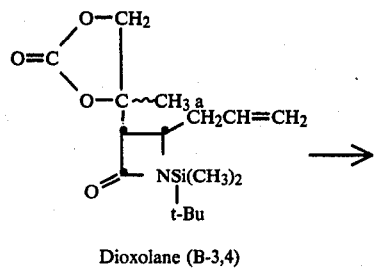

Dioxolane (B-3,4)

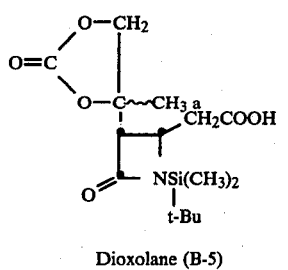

Dioxolane (B-5)

A solution of Dioxolane (B-3) (1.73 g) and mercuric acetate (1.92 g) in methanol (10 ml) is stirred at room temperature for 2 hours. This solution is added to a solution of cupric chloride dihydrate (3.09 g) and palladium chloride (120 mg) in methanol (20 ml), and the mixed solution is stirred at 60° C. for 1 hour. After cooling, the mixture is made alkaline with sodium hydrogen carbonate, filtered to remove solid and concentrated to dryness. The residue is purified by silica gel chromatography to give the captioned Dioxolane (B-5) (1.62 g) from the fraction eluted with a mixture of benzene and ethyl acetate (1:1).

EXAMPLE 31

1-t-Butyldimethylsilyl-3-(4-methyl-2-oxo-1,3-dioxolan-4-yl)-4-(2-oxopropyl)-2-azetidinone (B-6)

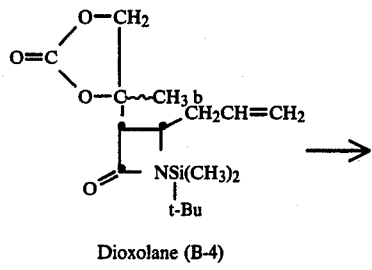

Dioxolane (B-4)

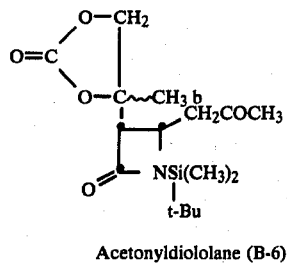

Acetonyldiololane (B-6)

A solution of Dioxolane (B-4) (1.6 g) and mercuric acetate (1.76 g) im methanol (10 ml) is stirred at room temperature for 2 hours. The solution is then added to a solution of cupprous chloride dihydrate (2.90 g) and palladium chloride (100 mg) in methanol (20 ml), and the mixed solution is stirred at 60° C. for 1 hour. After cooling, the reaction mixture is made alkaline with saturated aqueous sodium hydrogen carbonate, filtered to remove solid and concentrated to remove the solvent. The residue is extracted with ethyl acetate. The extract is washed with water, dried and concentrated. The residue is purified by silica gel chromatography to give the captioned Acetonyldioxolane (B-6) (1.2 g) from the fractions eluted with ethyl acetate-benzene (1:1) mixture.

EXAMPLE 32

α-[4-Allyl-3-(2-oxo-1,3-dioxolan-4-yl)-2-azetidinone-1-yl]glycolic acid pivaloyloxymethyl ester (D-2)

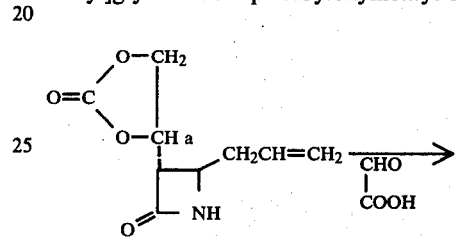

Lactam (C-1)

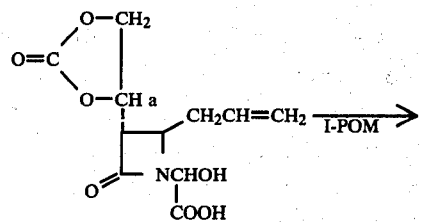

Glycolic acid (D-10)

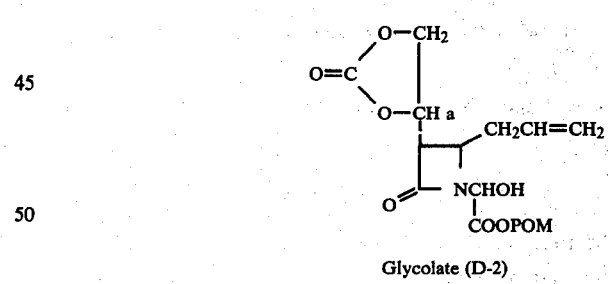

Glycolate (D-2)

To a solution of Lactam (C-1) (478 mg) in N,N-dimethylformamide (4 ml) are added glyoxylic acid (0.60 g) and Molecular Sieves 4 A (1.0 g), and the mixture is stirred overnight at room temperature. The reaction mixture is diluted with ethyl acetate, washed with saturated saline, dried and concentrated to give Glycolic acid (D-10) (707 mg). Oily material. This is dissolved in N,N-dimethylformamide (3.5 ml), potassium carbonate (168 mg) and iodomethyl pivalate I-POM (0.7 ml), and the mixture is stirred at room temperature for 15 minutes. The reaction mixture is poured into water, and extracted with ethyl acetate. The extract solution is washed with water, dried and concentrated. The residue is purified by silica gel chromatography to give the captioned Glycolate (D-2) (536 mg).

EXAMPLE 33

α-[4-Allyl-3-(4-methyl-2-oxo-1,3-dioxolan-4yl)-2-azetidinon-1-yl]glycolic acid pivaloyloxymethyl ester (D-3,4)

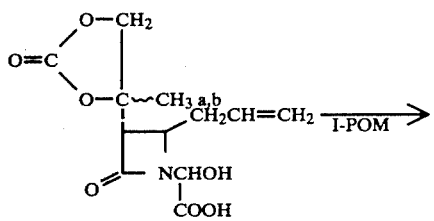

Glycolic acid (D-10,11)

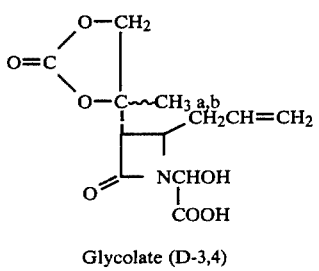

Glycolate (D-3,4)

To a solution of Glycolic acid (D-10) (330 mg) in N,N-dimethylformamide (1 ml) are added potassium carbonate (72 mg) and iodomethyl pivalate (I-POM) (0.4 g), and the mixture is stirred at room temperature for 2 hours. The reaction mixture is diluted with ethyl acetate, washed with aqueous sodium hydrogen carbonate containing sodium thiosulfate and saline, dried and concentrated to give the captioned Glycolate (D-3) (370 mg).

Under the same condition, Glycolic acid (D-11) (445 mg) gives Glycolate (D-4) (540 mg).

EXAMPLE 34

3-Methyl-6-(4-methyl-2-oxo-1,3-dioxolan-4-yl)-7-oxo-1-azabicyclo[3.2.0]-2-hepten-2-carboxylic acid pivaloyloxymethyl ester (F-10)

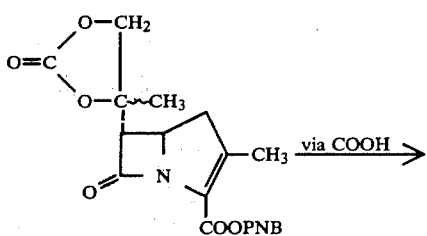

Carbapenem (F-9)

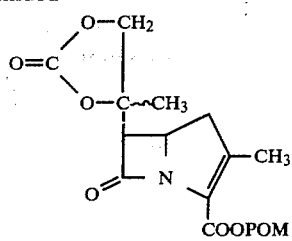

Carbapenem ester (F-10)

Carbapenem(F-9) (20 mg) in ethyl acetate (4 ml) is hydrogenated in hydrogen atmosphere in the presence of 5% palladium carbon (20 mg). After 1 hour, 5% palladium carbon (10 mg) is added and the mixture is stirred for further 2 hours. Solid is removed by filtration from the mixture and the filtrate is concentrated to give the corresponding carboxylic acid of the captioned Carbapenem. This is dissolved in N,N-dimethylformamide (1 ml), cooled at −10° C., mixed with iodomethyl pivalate (50 mg) and triethylamine (5 μl), and stirred for 1 hour. The reaction mixture is diluted with ethyl acetate (10 ml), washed with saturated saline, dried and concentrated. The residue is purified by chromatography to give the captioned Carbapenem ester (F-10) (7 mg) from the fraction eluted with ethyl acetatebenzene mixture.

EXAMPLE 35

3-Methyl-6-(4-methyl-2-oxo-1,3-dioxolan-4-yl)-7-oxo-1-azabicyclo[3.2.0]hept-2-en-2-carboxylic acid sodium salt

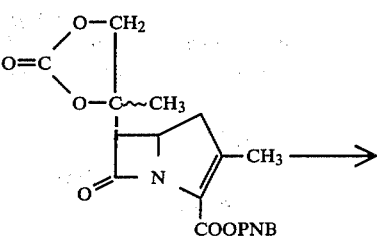

Carbapenem (F-9)

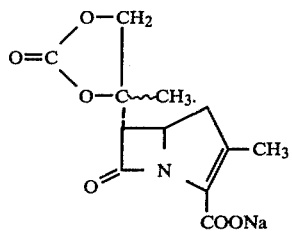

Carbapenemcarboxylic Acid Sodium salt (M-2)

To a solution of Carbapenem(F-9) (31 mg) and sodium hydrogen carbonate (51 mg) in a mixture of ethyl acetate and water (1:1) (8 ml) and the mixture is shaken under hydrogen in the presence of 5% palladium carbon (31 mg) to hydrogenate. After consuming hydrogen during 20 minutes, the reaction mixture is filtered to remove solid and water layer is taken up. This is lyophilized by a conventional manner to give the captioned Carboxylic acid sodium salt (M-2) (13 mg).

EXAMPLE 35A

3-Methyl-6-(4-methyl-2-oxo-1,3-dioxolan-4-yl)-7-oxo-1-azabicyclo[3.2.0]hept-2-en-2-carboxylic acid sodium salt (M-1)

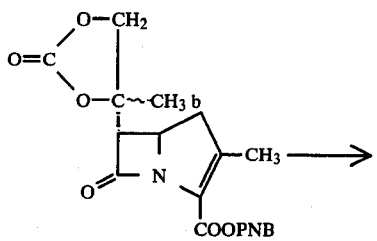

Carbapenem (F-10)

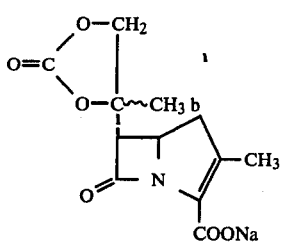

Carbapenem salt (M-1)

To a solution of Carbapenem (F 10) (20 mg) and sodium hydrogen carbonate (17 mg) in ethyl acetate-water (1:1 v/v) (8 ml) is added 5% pallacium charcoal (20 mg), and the mixture is shaken under hydrogen to hydrogenate the compound. Hydrogen (4.5 ml) is consumed at room temperature for 30 minutes. The r reaction mixture is filtered to remove solid and aqueous layer is separated. The layer is lyophilized to give the captioned Carbapenem sodium salt (M-1) (10 mg).

EXAMPLE 36

3-Acetamidoethylthio-6-(4-methyl-2-oxo-1,3-dioxolan-4-yl)-7-oxo-1-azabicyclo[3.2.0]heptan-2-carboxylic acid pivaloyloxymethyl ester (J-9).

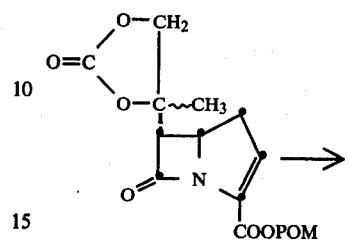

Penem ester (F-4)

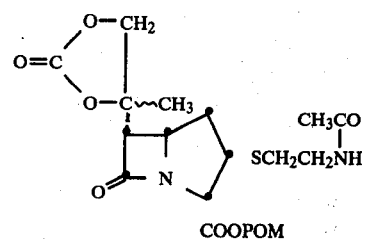

Penem ester (J-9)

To a solution of Penem ester (F-4) (368 mg) in a mixture of tetrahydrofuran (10 ml) and dimethylformamide (1.5 ml) are added N-acetylsysteamine (0.12 ml) and potassium carbonate (69 mg). After stirring at room temperature for 15 minutes, the solution is diluted with ethyl acetate, washed with water, aqueous sodiun hydrogen carbonate and saline, dried and concentrated. The residue is purified by reversed phase silica gel chromatography to give the captioned Penam ester (J-9) (522 mg) from the fractions eluted with acetonitrile. This is a mixture of stereoisomers in relation to the 2- and 3-positions.

EXAMPLE 37

3-Acetamidoethylthio-6-(4-methyl-2-oxo-1,3-dioxolan-4-yl)-7-oxo-1-azabicyclo[3.2.0]heptane-2-carboxylic acid p-nitrobenzyl ester (J-5,6,7)

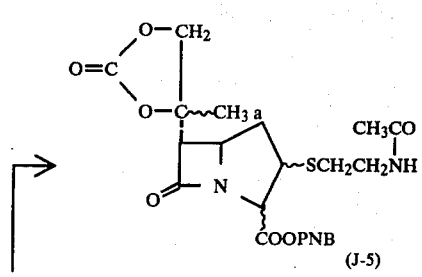

(J-5)

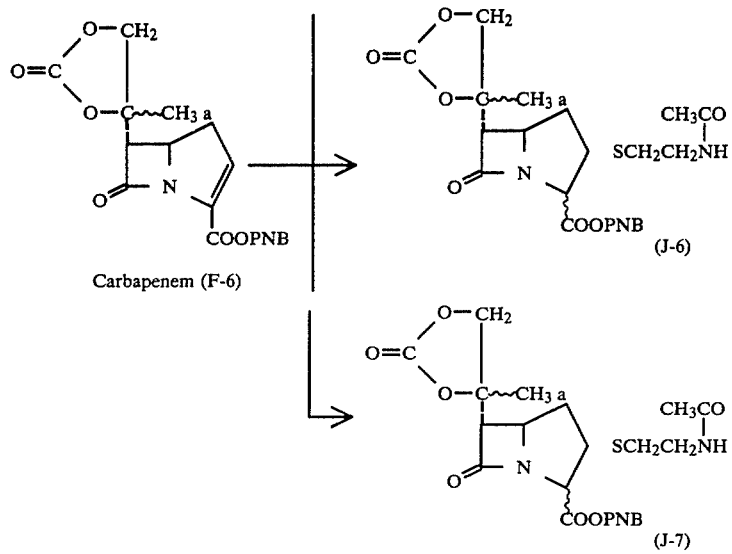

To a solution of Carbapenem (F-6) (194 mg) in a mixture of tetrahydrofuran (5 ml) and N,N-dimethylformamide (0.75 ml) are added N-acetylcysteamine (71 μl) and potassium carbonate (20 mg), and the mixture is stirred at room temperature for 2.5 hours. The reaction mixture is diluted with ethyl acetate, washed with water, dried and concentrated. The residue is separated by silica gel chromatography to give sulfides (J-5 to 7) from the fractions eluted with ethyl acetate in the order of lower polarity, J-5 (2β, 3β, 6α) (69 mg); J-6 (2α, 3β, 6α) (93 mg); and J-7 (2α, 3α, 6α) (68 mg).

EXAMPLE 38

3-Methylthio-6-(4-methyl-2-oxo-1,3-dioxolan-4-yl)-7-oxo-1-azabicyclo[3.2.0]heptan-2-carboxylic acid p-nitrogenzyl ester (J-1, 2, 3)

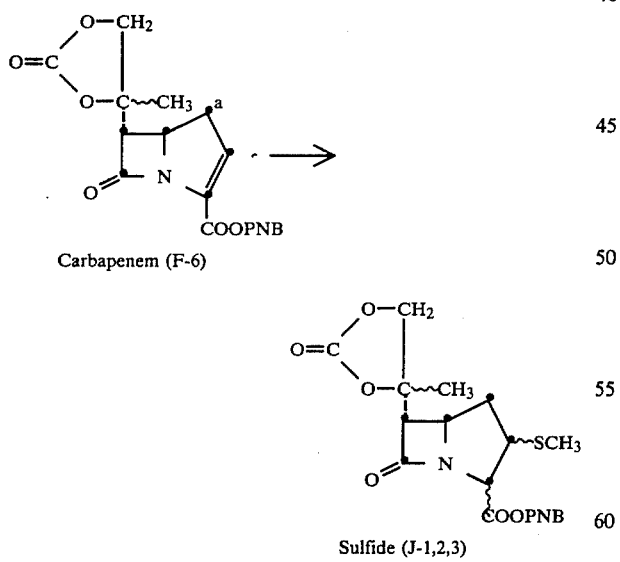

To a solution of Carbapenem (F-6) (163 mg) in a mixture of tetrahydrofuran (4.2 ml) and dimethylformamide (0.6 ml) are added potassium hydrogen carbonate (17 mg) and 30% methylmercaptane methanolic solution (0.134 ml) under ice cooling, and the mixture is stirred for 1 hour. The reaction mixture is diluted with dichloromethane, washed with water, dried and evaporated. The residue is purified by silica gel chromatography to give the captioned Sulfides(J-1 to 3) as stereoisomers J-1 (2β, 3β, 6β) (90 mg); J-2 (2α, 3α, 6α) (57 mg; and J-3) (2α, 3α, 6α) (47 mg). from the fractions eluted with ethyl acetate-benzene (1:1 to 1:2) mixtures.

EXAMPLE 39

6-(4-Methyl-2-oxo-1,3-dioxolan-4-yl)-3-methylthio-7-oxo-1-azabicyclo[3.2.0]hept-2-en-2-carboxylic acid p-nitrobenzyl ester (F-12)

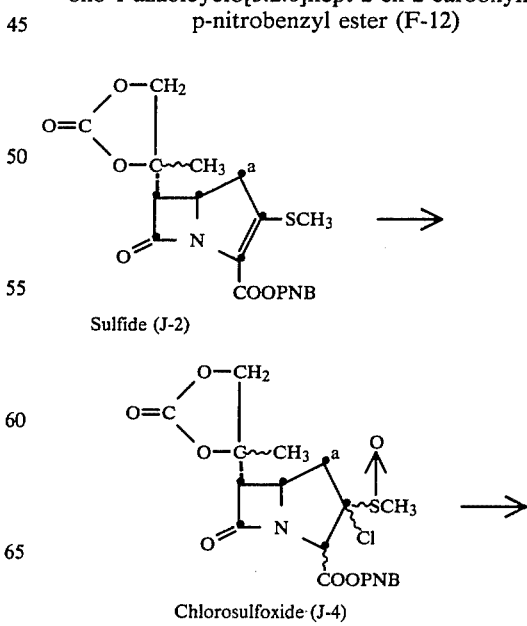

-continued

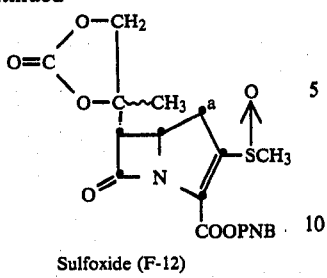

Sulfoxide (F-12)

To a solution of Sulfide (J-2) (90 mg) in chloroform (82 ml) are added pyridine (58 μl) and water (29 μl) under ice cooling, and then iodobenzene dichloride (130 mg), and the mixture is stirred for 2 hours. The reaction mixture is evaporated to leave a residue which is chromatographed over silica gel to give Chlorosulfoxide (J-4) (58 mg) from the fraction eluted with ethyl acetate and that with chloroform-acetonitrile mixture (1:1). Fourty seven milligram of the Chlorosulfoxide is dissolved in acetonitrile (0.5 ml), mixed with triethylamine (16 μl) and allowed to stand at room temperature for 1 hour. The reaction mixture is diluted with dichloromethane (5 ml), washed with water, dried and concentrated. The residue is purified by silica gel chromatography to give the captioned Sulfoxide (F-12) (39 mg).

EXAMPLE 40

6-(1-Hydroxymethylethylidene)-3-methylthio-7-oxo-1-azabicyclo[3.2.0]hept-2-ene-2-carboxylic acid p-nitrobenzyl ester sulfoxide (G-7)

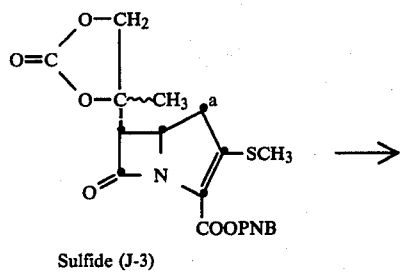

Sulfide (J-3)

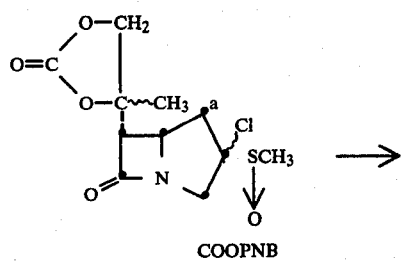

Chlorosulfoxide (J-5)

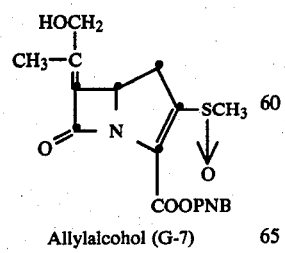

Allylalcohol (G-7)

The sulfide (J-3) (47 mg) is treated with iodobenzene dichloride (2 mole equivalents) in a manner similar to the preceding Example 39 to give the corresponding Chlorosulfoxide (J-5) (32 mg), and the latter is treated with DBU (1 mole equivalent or more) to give allyl alcohol (G-8) (10 mg).

EXAMPLE 41

6-(1-Hydroxymethylethylidene)-3-methylthio-7-oxo-1-azabicyclo[3.2.0]hept-2-en-2-carboxylic acid p-nitrobenzyl ester sulfoxide (G-7,8)

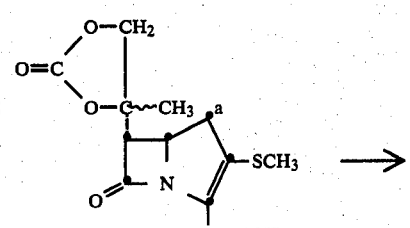

Sulfide (J-1)

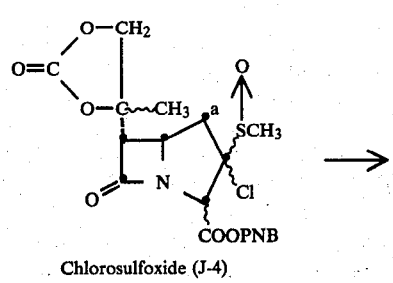

Chlorosulfoxide (J-4)

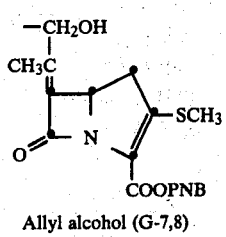

Allyl alcohol (G-7,8)

Sulfide (J-1)(57 mg) is treated with iodobenzene dichloride (2 equivalents) in a manner similar to the preceding Example to give Chlorosulfoxide (J-4)(46 mg), and the latter is treated with DBU (1 equivalent or more) to give Allyl alcohol (a mixture of G-7 and G-8)(16 mg). These are the epimers in relation to the sulfoxide S→O bond. The mixture can be separated to give pure isomers by silica gel chromatography.

EXAMPLE 42

3-Acetoamidoethylthio-6-(4-methyl-2-oxo-1,3-dioxolan-4-yl)-7-oxo-1-azabicyclo[3.2.0]hept-2-en-2-carboxylic acid p-nitrobenzyl ester sulfoxide (F-14)

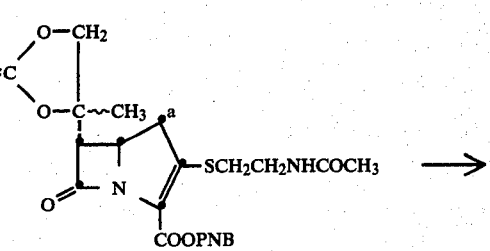

Sulfide (J-7)

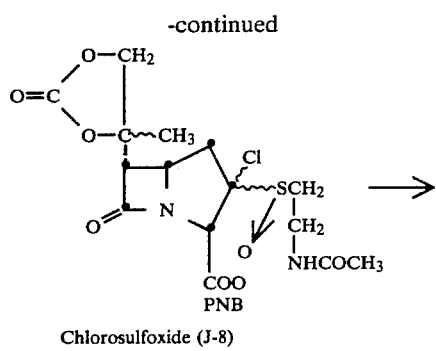

Chlorosulfoxide (J-8)

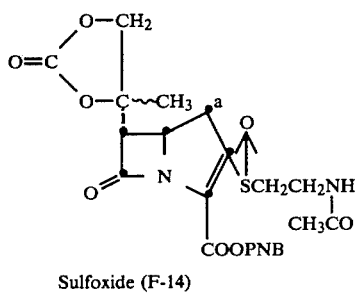

Sulfoxide (F-14)

To a solution of Sulfide (J-7)(68 mg) in chloroform (5.4 ml) are added pyridine (40 μl) and water (20 μl) and after ice cooling, iodobenzene dichloride (80 mg). After 3 hours stirring, the reaction mixture is extracted with ethyl acetate to give Chlorosulfoxide (J-8)(47 mg). This is dissolved in acetonitrile (1.7 ml), mixed with triethylamine (14 μl) and stirred at room temperature for 3 hours. The reaction mixture is concentrated. The residue is triturated in ether to give the captioned Sulfoxide (F-14)(13 mg).

EXAMPLE 43

3-Acetamidoethylthio-6-(4-methyl-2-oxo-1,3-dioxolan-4-yl)-7-oxo-1-azabicyclo[3.2.0]hept-(2 or 3)-en-2-carboxylic acid pivaloyloxymethyl ester (K-2, F-15)

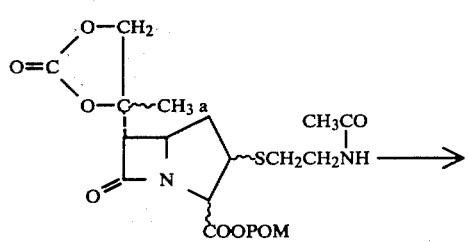

Penam ester (J-9)

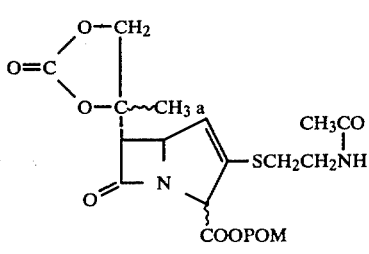

Carbapenam (K-2)

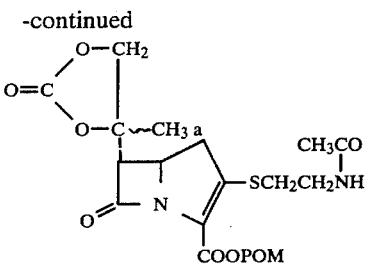

Carbapenem (F-15)

Under the condition similar to the case of p-nitrobenzyl ester, Penam ester (J-9)(439 mg) is treated with m-chloroperbenzoic acid (183 mg) under ice cooling for 10 minutes to give the corresponding Sulfoxide (411 mg).

This is treated with thionyl chloride (72 μl) and pyridine (230 μl) in dichloromethane (8.2 μl) under ice cooling for 30 minutes. The product is isolated in a conventional manner to give the captioned Carbapenem (F-15)(49 mg) and non-conjugated Carbapenem (K-2)(236 mg).

EXAMPLE 44

3-Acetamidoethylthio-6-(4-methyl-2-oxo-1,3-dioxolan-4-yl)-7-oxo-1-azabicyclo[3.2.0]hept-3-en-2-carboxylic acid p-nitrobenzyl ester (K-1)

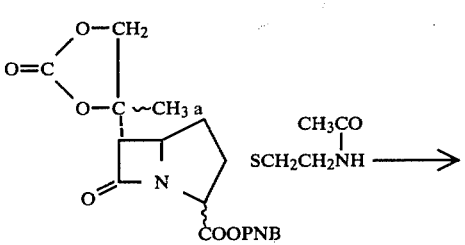

c(3βS,2βCOB)(J-5)
d(3βS,2αCOB)(J-6)
e(3λS,2αCOB)(J-7)

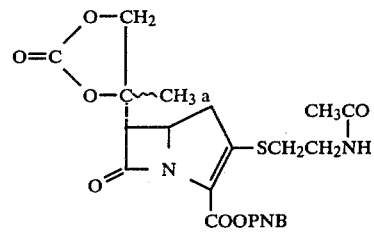

(K-1) + (J-6) = d

To a solution of Carbapenam (mixture of J-5 to 7)(910 mg) in dichloromethane (30 ml) is added m-chloro-perbenzoic acid (312 mg) under ice cooling. After stirring for 30 minutes, the reaction mixture is washed with sodium hydrogen carbonate and saline, dried and concentrated to give the corresponding mixture of Sulfoxides (stereoisomer mixture)(869 mg). This is dissolved in dichloromethane (15 ml), mixed with pyridine (410 μl) and thionyl chloride (150 μl) under ice cooling, mixed with ice water and dichloromethane after 30 minutes, shaken and the organic layer separated. The dichloromethane layer is washed with aqueous sodium hydrogen carbonate and saline, dried and concentrated. The residue is separated by silica gel chromatography to give non-conjugated Carbapenem (K-1)(322 mg) and one of the stereoisomers in the starting material (J-6)(63 mg recovery) from the fraction eluted with 15% isopropanol-ethyl acetate.

EXAMPLE 45

3-Acetamidoethylthio-6α-(4-methyl-2-oxo-1,3-dioxolan-4-yl)-7-oxo-1-azabicyclo[3.2.0]hept-2-en-2-carboxylic acid p-nitrobenzyl ester (F-16)

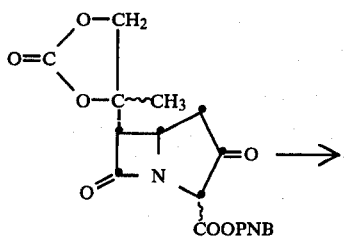

Carbapenam (F-9)

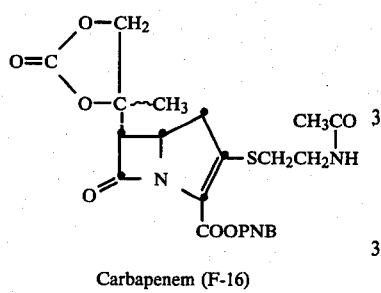

Carbapenem (F-16)

To a suspension of Carbapenam (F-9)(53 mg) in acetonitrile (7 ml) are added diphenylchlorophosphate (30 μl) and diisopropylethylamine (25 μl) under ice cooling. After 10 minutes stirring, the solution of produced enol chloride is mixed with diisopropylethylamine (30 μl) and N-acetylcysteamine (15 μl) under ice cooling. After 50 minutes stirring, the reaction mixture is diluted with ethyl acetate (100 ml), washed with water, dried and concentrated. The residue is purified by silica gel chromatography to give the captioned Carbapenem (F-16)(49 mg).

EXAMPLE 46

6-(2-Hydroxyethylidene)-7-oxo-1-azabicyclo[3.2.0-]hept-2-en-2-carboxylic acid pivaloyloxymethyl ester (G-1)

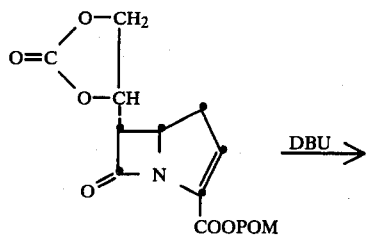

Carbapenem (F-3)

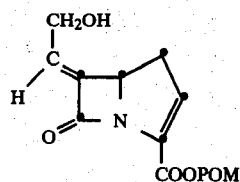

Allyl alcohol (G-1)

To a suspension of Carbapenem (F-3)(10 mg) in chloroform (0.5 ml) is added a solution of 1,5-diazabicyclo[5,4,0]undec-5-ene in toluene (1N, 3 μl). After stirring at room temperature for 5 minutes, the reaction mixture is poured into water and extracted with ethyl acetate. The extract solution is washed with water, dried and concentrated to give the captioned Allylalcohol (G-1)(8 mg).

EXAMPLE 47

6-(2-Hydroxyethylidene)-7-oxo-1-azabicyclo[3.2.0-]hept-2-en-2-carboxylic acid p-nitrobenzyl ester (G-1)

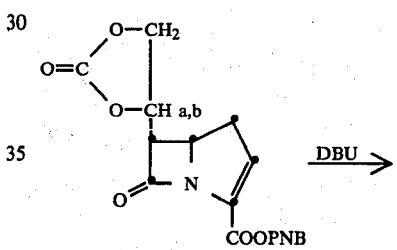

Carbapenem (F-1,2)

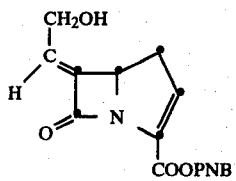

Allyl alcohol (G-1)

To a suspension of Carbapenem (F-1)(33 mg) in dichloromethane (1 ml) is added 1,5-diazabicyclo[5.4.-0]undec-5-ene(DBU) in toluene (1N, 10 μl). After 10 minutes stirring at room temperature, there results a clear solution. The solution is diluted with ethyl acetate immediately, washed with water, dried and concentrated to give Allyl alcohol (G-1)(28 mg).

Under the same condition Carbapenem (F-2)(32 mg) is treated with 1M-DBU solution in toluene (10 μl) under ice cooling in acetonitrile (1.0 ml). After stirring for 10 minutes, the reaction mixture is treated and worked up in the same manner as in the case of preceding isomer a to give Allyl alcohol (G-1) (30 mg).

EXAMPLE 48

6-(2-Hydroxy-1-methylethylidene)-7-oxo-1-azabicyclo[3.2.0]hept-2-en-2-carboxylic acid esters (G-3,4)

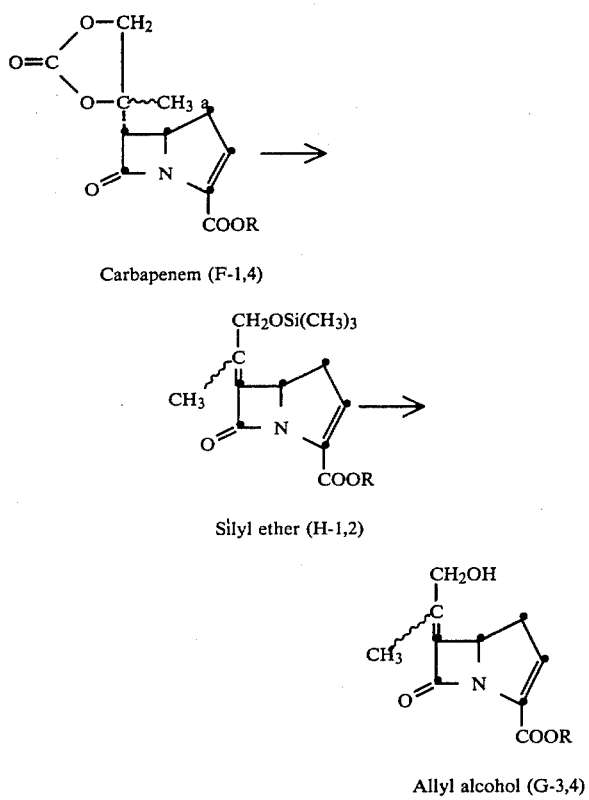

Carbapenem (F-1,4)

Silyl ether (H-1,2)

Allyl alcohol (G-3,4)

(1) Pivaloyloxymethyl ester.

To a solution of Carbapenem(F-4)(R=pivaloyloxymethyl)(110 mg) in dichloromethane (1.5 ml) is added O,N-bistrimethylsilylacetamide (0.073 ml). After 5 minutes stirring at room temperature, the solution is mixed with a solution of 1,5-diazabicyclo[5.4.0]undec-5-ene in toluene (1M, 0.03 µl). After 6 minutes, the reaction mixture is passed through silica gel and the column is washed with a mixture of n-hexane and ethyl acetate (1:1) and a mixture of dichloromethane and ethyl acetate (1;1). The eluted solution is concentrated to give Silyl ether (H-1)(135 mg) and Allyl alcohol (G-3)(34 mg), respectively.

The Silyl ether (H-1)(135 mg) is dissolved in tetrahydrofuran (1 ml), mixed with tetraethylammonium chloride (76 mg), and stirred at room temperature for 1 hour. The reaction mixture is diluted with ethyl acetate (20 ml), filtered to remove solid, and concentrated. The residue is purified by passing through a column of silica gel to give the captioned Allyl alcohol (G-3)(48 mg) in a manner similar to that of the preceding paragraph.

(2) p-Nitrobenzyl ester

To a solution of Carbapenem (F-1)(R=p-nitrobenzyl)(78 mg) in a mixture of acetonitrile and dichloromethane (1:1)(4 ml) is added O,N-bistrimethylsilylacetamide and 1,5-diazabicyclo[5.4.0]undec-5-ene and treated in a similar manner as the corresponding pivaloyloxymethyl ester to give Silyl ether (H-2)(45 mg) and the captioned Allyl alcohol (G-4)(14 mg).

The Silyl ether (H-2)(74 mg) is hydrolyzed in a manner similar to the preceding part to give the captioned Allyl alcohol (G-4)(40 mg) in 66%.

EXAMPLE 49

6-(2-Hydroxy-1-methylethylidene)-7-oxo-3-methyl-1-azabicyclo[3.2.0]hept-2-en-2-carboxylic acid pivaloyloxymethyl ester (G-6)

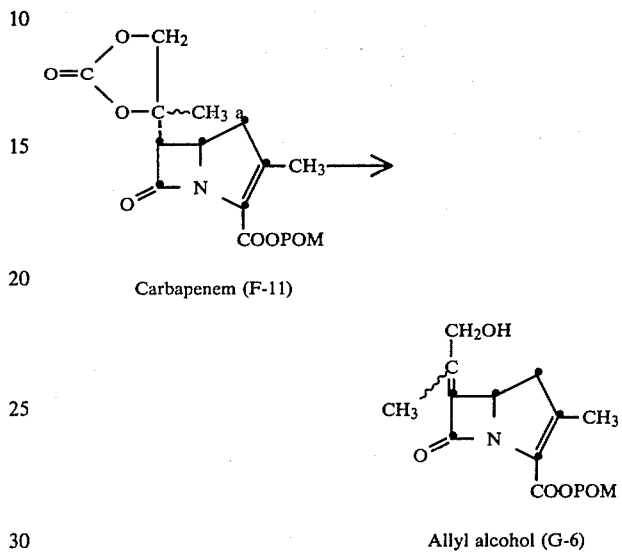

Carbapenem (F-11)

Allyl alcohol (G-6)

To a solution of Carbapenem (F-11)(7 mg) in chloroform (0.5 ml) is added a solution of 1,5-diazabicyclo[5.4.0]undec-5-ene (1 mole equivalent) in toluene at room temperature. After 2 minutes, the reaction mixture is diluted with ethyl acetate (5 ml), washed with saline, dried and concentrated to give the captioned Allyl alcohol (G-6)(1 mg).

EXAMPLE 50

6-(2-Hydroxy-1-methylethylidene)-7-oxo-3-methyl-1-azabicyclo[3.2.0]hept-2-ene-2-carboxylic acid p-nitrobenzyl ester (G-5)

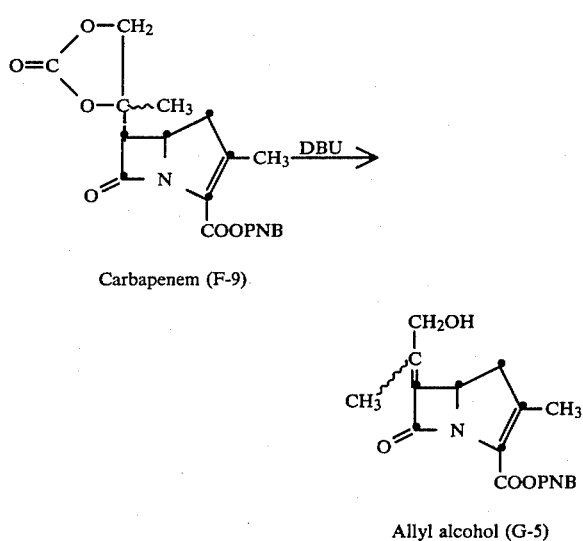

Carbapenem (F-9)

Allyl alcohol (G-5)

To a solution of Carbapenem (F-9)(50 mg) in chloroform (1 ml) is added 1,5-diazabicyclo[5.4.0]undec-5-ene (1M solution in toluene) (5 μl). After 1 minute at room temperature, the reaction mixture is diluted with ethyl acetate (5 ml), washed with saturated saline, dried and concentrated. The residue is the captioned Allyl alcohol (G-5).

EXAMPLE 51

6-(2-Hydroxy-1-methylethylidene)-3-methylthio-7-oxo-1-azabicyclo[3.2.0]hept-2-ene-2-carboxylic acid p-nitrobenzyl ester sulfoxide (G-7)

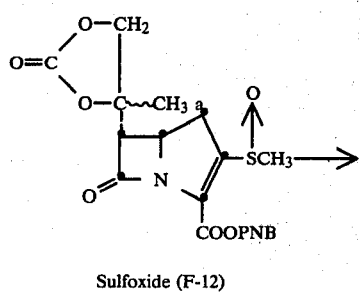

Sulfoxide (F-12)

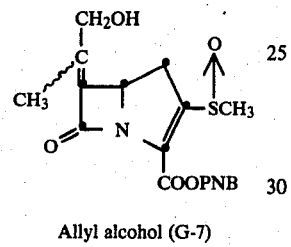

Allyl alcohol (G-7)

To a solution of Sulfoxide (F-12)(12 mg) is added a solution of 1,5-diazabicyclo[5.4.0]undec-5-ene in toluene (1M)(2.7 μl). After 15 minutes at room temperature, the reaction mixture is diluted with ethyl acetate, washed with water, dried and concentrated. The residue (15 mg) is purified by silica gel chromatography to give the captioned Allyl alcohol (G-7)(4 mg).

EXAMPLE 52

3-Acetamidoethylthio-6-(2-hydroxy-1-methylethylidene)-7-oxo-1-azabicyclo[3.2.0]hept-2-en-2-carboxylic acid p-nitrobenzyl ester (G-10)

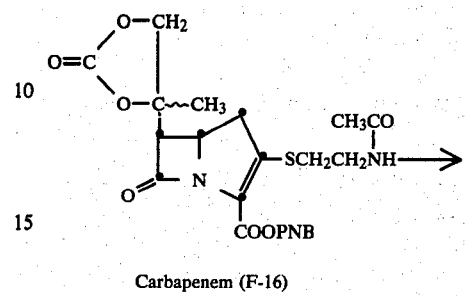

Carbapenem (F-16)

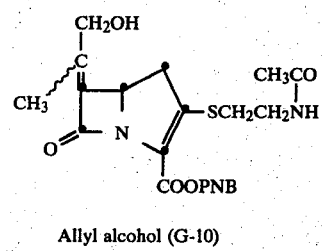

Allyl alcohol (G-10)

To a solution of Carbapenem (F-16)(31 mg) in deuterioacetonitrile is added a solution of 1,5-diazabicyclo[5.4.0]undec-5-ene in toluene (1M, 12 μl). The reacted solution is diluted with ethyl acetate (30 ml), washed with water, dried and concentrated. The residue is purified by silica gel chromatography to give Allyl alcohol (G-10)(10 mg) as captioned above.

EXAMPLE 53

3-Acetamidoethylthio-6-(2-hydroxy-1-methylethylidene)-7-oxo-1-azabicyclo[3.2.0]hept-2-en-2-carboxylic acid p-nitrobenzyl ester (G-10)

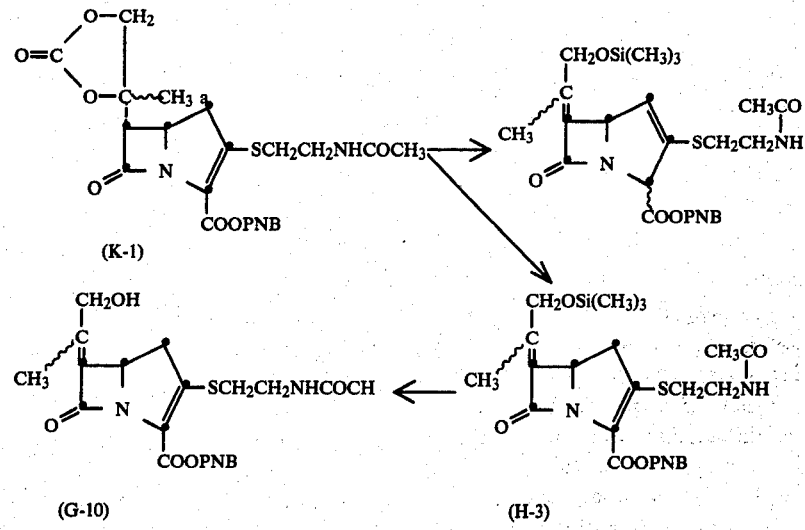

(1) To a solution of Carba-1-penem (K-1)(257 mg) in dichloromethane (2.5 ml) are added O,N-bistrimethylsilylacetamide (137 μl) and 1,5-diazabicyclo[5.4.0]undec-5-ene (25 μl). After 2 hours, the reaction mixture is subjected to silica gel chromatography to give Allyl alcohol silyl ether (H-3)(171 mg) and its non-conjugated position isomer (32 mg) from the fraction eluted with a mixture of n-hexane-dichloromethane-ethyl acetate-acetonitrile (1:1:1:1).

(2) To a solution of Allyl alcohol silyl ether (H-3)(171 mg) in a mixure of methanol (1.5 ml) and water (0.15 ml) is let stand at room temperature for 3 hours. By concentrating the solution, the reaction mixture is freed from the solvents. The residue is triturated in a mixture of dichloromethane and ether to give Allyl alcohol (G-10)(64 mg).

EXAMPLE 54

3-Acetamidoethylthio-6-(2-hydroxy-1-methylethylidene)-7-oxo-1-azabicyclo[3.2.0]hept-(2 or 3)-ene-2-carboxylic acid pivaloyloxymethyl ester (K-1, G-11)

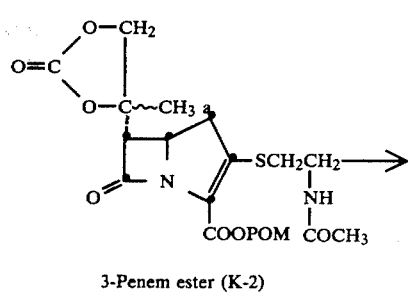

3-Penem ester (K-2)

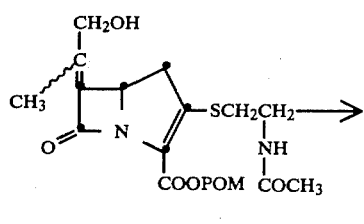

(H-4)

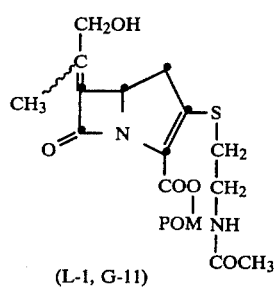

(L-1, G-11)

In a manner similar to the corresponding p-nitrobenzyl ester non-conjugated Carbapenem ester (K-2)(164 mg) is treated with O,N-bistrimethylsilylacetamide (165 μl) and 1,5-diazabicyclo[5.4.0]undec-5-ene (17 μl) in dichloromethane to give Silyl ether (H-4) and its double bond position isomer (totally, 170 mg).

The silylated compound mixture (170 mg) is dissolved in a mixture of methanol (0.4 ml) and water (40 μl). After 3 hours at room temperature, the reaction mixture is worked up as usual and the residue is separated by silica gel chromatography to give the captioned Allyl alcohols isomers, conjugated Carbapenem (G-11)(26 mg) and non-conjugated Carbapenem derivative (L-1)(29 mg).

EXAMPLE 55

3-Acetamidovinylthio-6-(2-hydroxy-1-methylethylidene)-7-oxo-1-azabicyclo[3.2.0]hept-2-en-2-carboxylic acid p-nitrobenzyl ester sulfoxide (G-9 sulfoxide)

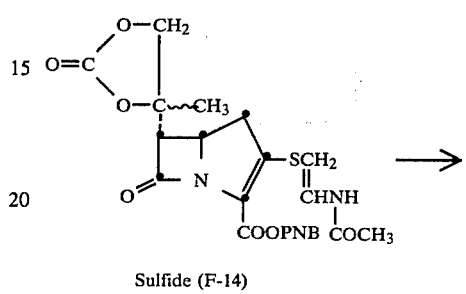

Sulfide (F-14)

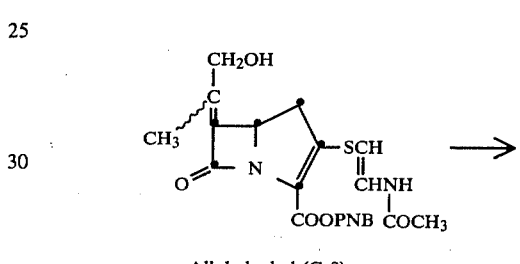

Allyl alcohol (G-9)

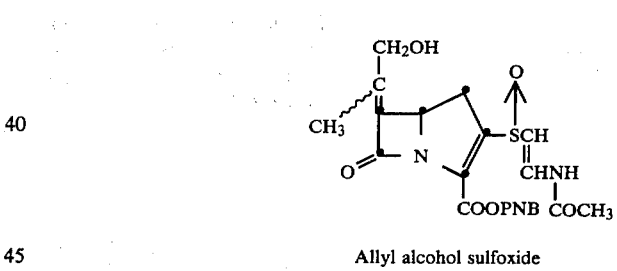

Allyl alcohol sulfoxide

To a solution of Sulfide (F-14)(14 mg) in dichloromethane (0.6 ml) is added 1,5-diazabicyclo[5.4.0]undec-5-ene in toluene (1M)(6 μl). After 10 minutes, the reaction mixture is passed rapidly through a column of silica gel to give Allyl alcohol (G-9) from the fraction eluted with a mixture of n-hexane, dichloromethane, ethyl acetate, and acetonitrile (1:1;1:1). A part of this product (0.25 mg) is dissolved in dichloromethane (0.25 ml), mixed with 0.05M-m-chloroperbenzoic acid dichloromethane solution (0.01 ml). After stirring for 30 minutes, the reaction mixture is checked by thin-layer chromatography and high precision liquid chromatography to identify with the esterified natural asparenomycin.

EXAMPLE 56

3-Acetamidovinylthio-6-(2-oxo-4-methyl-1,3-dioxolan-4-yl)-1-azabicyclo[3.2.0]hept-2-en-2-carboxylic acid p-nitrobenzyl ester (F-17)

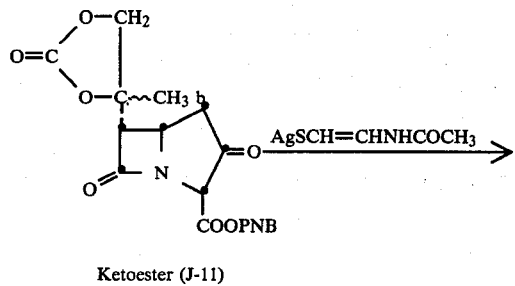

Ketoester (J-11)

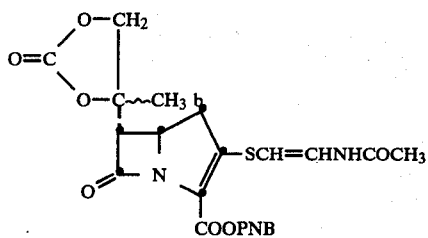

Thioether (F-17)

To a suspension of Ketoester (J-11)(70 mg) in acetonitrile (5 ml) are added diphenyl chlorophosphate (40 μl) and diisopropyl ethylamine (33 μl) under ice cooling. After stirring for 10 minutes, (E)-2-acetamido-1-ethenylthiolate silver salt (58 mg) and sodium iodide (37 mg) are added to the mixture. After stirring at room temperature for 25 hours, the reaction mixture is diluted with ethyl acetate, washed with water, dried and concentrated. The residue is purified by silica gel chromatography to give the captioned Thiolate (F-17)(57 mg).

EXAMPLE 57

3-Acetamidovinylthio-6-(2-oxo-4-methyl-1,3-dioxolan-4-yl)-1-azabicyclo[3.2.0]hept-2-en-2-carboxylic acid sodium salt (M-3)

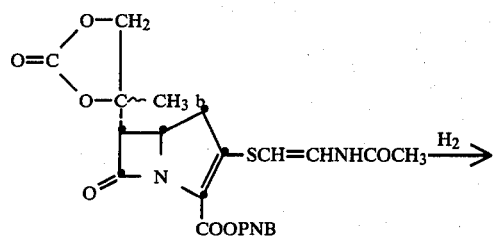

Thioether (F-17)

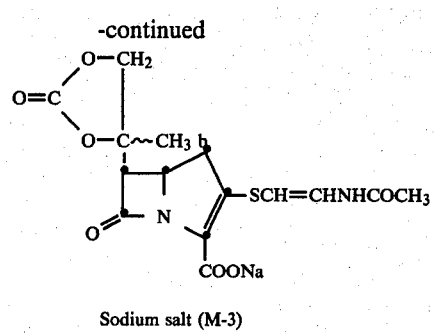

Sodium salt (M-3)

In a mixture of dioxane (2 ml) and 0.02M-phosphate, buffer (pH 7)(5 ml), 10% palladium carbon (100 mg) is shaken under hydrogen atmosphere for 30 minutes. To this mixture is added a solution of Thioester (F-17)(52 mg) in a mixture of dioxane (8 ml) and tetrahydrofuran (7 ml). After hydrogenation at room temperature under atmospheric pressure for 4 hours, the reaction mixture is passed through a layer of Hyflo Super Cel to remove the catalyzer and the solution is concentrated under reduced pressure to remove the solvent. The remaining water layer is washed with ethyl acetate and poured onto a column of Diaion HP-20AG (produced by Mitsubish Chemical Co.). The column is washed with 5% saline (100 ml) and then water to elute the product. The fraction containing the product is gathered and concentrated. Lyophilizating the solution gives the Sodium salt as white solid (27 mg) (M-3).

EXAMPLE 58

3-Acetamidovinylthio-6-(1-hydroxy-2-propylidene)-1-azabicyclo[3.2.0]hept-2-en-2-carboxylic acid sodium salt (G-13)

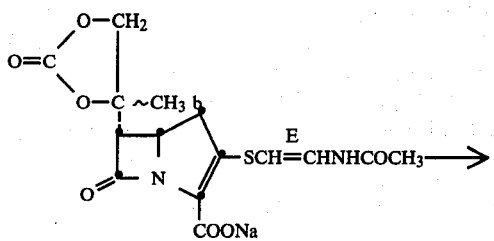

Sodium salt (M-3)

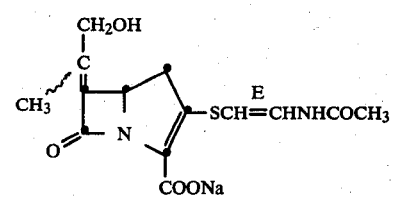

Allyl alcohol (G-13)

Sodium salt (M-3)(17 mg) in deuterium oxide (0.5 ml) is mixed sodium hydrogen carbonate (18 mg). After 5 hours at room temperature, the mixture is kept at 0° C. for 15 hours. The reaction mixture is subjected to high precision liquid chromatography (Nucleosil 5-$C_{18}$; 10×300 mm; 0.05M phosphate buffer-10% methanol) to collect the fraction containing the product. This is passed through Diaion HP-20AG(Mitsubish Chemical Co.) to deionize and then lyophilized to give Allyl alcohol (G-13)(7 mg) as colorless powder.

This compound is identical with a natural product, Asparenomycin C when identified by high precision liquid chromatography and nuclear magnetic resonance spectrometry.

TABLE A

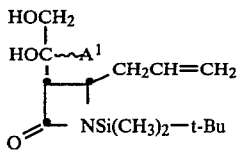

| No. | $A^1$ | IR: $\nu_{max}^{CHCl_3}$ | NMR: $\delta_{ppm}^{CDCl_3}$ (Hz value = J value) | Ex. No. |
|---|---|---|---|---|
| 1 | a-H | 1710 | 0.23s3H, 0.27s3H, 1.00s9H, 1.9–3.3m4H, 3.5–4.0brm5H, 4.9–6.2m3H. | 3 |
| 2 | b-H | 1720 | 0.23s3H, 0.27s3H, 0.97s9H, 2.0–3.0m3H, 3.2–4.3m5H, 4.9–6.1m3H. | 3 |
| 3 | a-CH$_3$ | | 0.23s3H, 0.30s3H, 1.00s9H, 1.08s3H, 2.2–2.8m2H, 2.85d(2Hz)1H, 3.0–4.7m5H, 5.0–6.2m3H. | 2 |
| 4 | b-CH$_3$ | | 0.23s3H, 0.27s3H, 1.00s9H, 1.30s3H, 1.9–4.0m8H, 4.9–6.2m3H. | 2 |

TABLE B

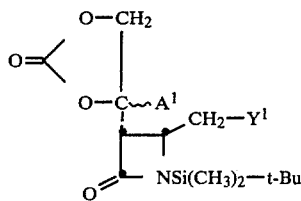

| No. | $A^1$ | $Y^1$ | NMR: $\delta_{ppm}^{CDCl_3}$ (Hz value = J value) | IR: $\nu_{max}^{CHCl_3}$ cm$^{-1}$ | Ex. No. |
|---|---|---|---|---|---|
| | | | (Part 1) | | |
| 1 | a-H | —CH=CH$_2$ | 0.23s3H, 0.28s3H, 1.00s9H, 1.9–2.9m2H, 3.13t(3Hz)1H, 3.47–3.78m1H, 4.0–6.2m6H. | 1740, 1810. | 4 |
| 2 | b-H | —CH=CH$_2$ | 0.25s3H, 0.30s3H, 1.00s9H, 2.0–2.95m2H, (3.10d + 3.22d)dd(2Hz)1H, 3.47–3.78m1H, 4.0–6.2m6H. | 1740, 1810. | 4 |
| 3 | a-CH$_3$ | —CH=CH$_2$ | 0.23s3H, 0.30s3H, 1.00s9H, 1.33s3H, 2.0–2.95m2H, 3.10d(3Hz)1H, 3.50–3.83 m1H, (4.07d + 4.67d)ABq(8Hz)2H, 5.0–6.2 m3H(CCl$_4$). | | 5 |
| 4 | a-CH$_3$ | —CO—CH$_3$ | 0.23s3H, 0.27s3H, 1.00s9H, 1.62s3H, 2.15–2.95m2H, 3.17d(3Hz)1H, 3.43–3.73 m1H, (4.10d–4.33d)ABq(8Hz)2H, 5.0–6.2 m3H. | 1780, 1810. | 30 |
| | | | (Part 2) | | |
| 5 | a-CH$_3$ | —CO—CH$_3$ | 0.27s3H, 0.30s3H, 1.00s9H, 1.60s3H, 2.20s3H, 2.96m2H, 3.16d(2Hz)1H, 3.91dd(4;2Hz)1H, (4.13d + 4.77d)ABq (8Hz)2H. | 1780, 1810. | 30 |
| 6 | b-CH$_3$ | —CO—CH$_3$ | 0.23s3H, 0.27s3H, 0.97s9H, 1.67s3H, 2.20s3H, 2.90m2H, 3.20d(2.5Hz)1H, 3.80m1H, (4.13d + 4.77d)ABq(8Hz)2H. | | 31 |
| 7 | b-CH$_3$ | —CO—OH | 0.27s3H, 0.29s3H, 0.99s9H, 1.66s3H, 2.2–3.2m2H, 3.44d(3Hz)1H, 3.7–4.2m1H, (4.14d + 4.61d)ABq(9Hz)2H, 9.59brs1H. | 3500–2400, 1805, 1740, 1720sh. | 25 |

TABLE C

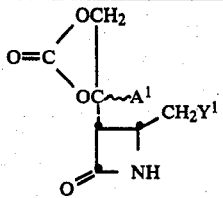

| No. | A¹ | Y¹ | NMR:$\delta_{ppm}^{CDCl_3}$ (Hz value = J value) | IR:$\nu_{max}^{CHCl_3}$ | Ex. No. |
|---|---|---|---|---|---|
| | | | (Part 1) | | |
| 1 | a-H | —CH=CH₂ | 2.43t(6Hz)2H, 3.17t(2Hz)1H, 3.6–6.1m7H, 6.6br1H. | 1770, 1810. | 6 |
| 2 | b-H | —CH=CH₂ | 2.43t(6Hz)2H, (3.07d + 3.20d)dd(2Hz)1H, 3.53–3.83m1H, 4.2–6.2m6H, 6.9br1H. | 1770, 1820. | 6 |
| 3 | a-CH₃ | —CH=CH₂ | 1.55s3H, 2.45t(6Hz)2H, 3.07d(2Hz)1H, 3.60–3.87m1H, (4.13d + 4.68d)ABq(8Hz)2H, 4.9–6.1m3H, 6.6br1H. | | 7 |
| 4 | b-CH₃ | —CH=CH₂ | 1.00s3H, 2.47t(6Hz)2H, 3.12d(2Hz)1H, 3.53–3.80m1H, (4.17d + 4.40d)ABq(8Hz)2H, 4.9–6.2m3H, 6.5br1H. | | 7 |
| | | | (Part 2) | | |
| 5 | a-CH₃ | —CO—CH₃ | 1.60s3H, 2.17s3H, 2.83d(4Hz)1H, 3.00m2H, 3.93dd(4;2Hz)1H(4.13d + 4.67d)ABq(8Hz)2H, 6.67br1H. | | 8 |
| 6 | b-CH₃ | —CO—CH₃ | 1.67s3H, 2.17s3H, 2.83d(4Hz)1H, 3.06m2H, 3.87m1H, (4.17d + 4.53d)ABq(9Hz)2H, 6.57br1H. | | 9 |
| 7 | b-CH₃ | —CO—CH₂—CO₂—PNB | 1.66s3H, 2.9–3.4m2H, 3.23d(2Hz)1H, 3.65s2H, 3.7–4.1m1H, (4.18d + 4.52d)ABq(9Hz)2H, 5.29s2H, 6.73brs1H, (7.55d + 8.23d)q(9Hz)4H. | 3400, 1805, 1765, 1750sh, 1710. | 26 |
| 8 | b-CH₃ | —CO—CN₂—CO₂—PNB | 1.66s3H, 3.1–3.4m3H, 3.8–4.1m1H, (4.17d + 4.50d)ABq(9Hz)2H, 5.38s2H, 6.55brs1H, (7.55d + 8.27d)q(9Hz)4H. | 3400, 2145, 1810, 1775, 1720, 1665. | 27 |

TABLE D

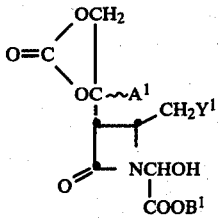

| No. | A¹ | Y¹ | B¹ | NMR:$\delta_{ppm}^{CDCl_3}$ (Hz value = J value) | IR:$\nu_{max}^{CHCl_3}$ | Ex. No. |
|---|---|---|---|---|---|---|
| | | | | (Part 1) | | |
| 1 | a-H | —CH=CH₂ | PNB | | 1360, 1770, 1810. | 12 |
| 2 | a-H | —CH=CH₂ | POM | 1.22s9H, 2.08–2.78m2H, 3.20–3.42m1H, 3.77–4.22m1H, 4.40–6.10m10H. | 1760, 1815, 3500. | 32 |

TABLE D-continued

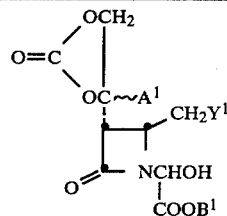

| No. | $A^1$ | $Y^1$ | $B^1$ | NMR:$\delta_{ppm}^{CDCl_3}$ (Hz value = J value) | IR:$\nu_{max}^{CHCl_3}$ | Ex. No. |
|---|---|---|---|---|---|---|
| 3 | a-CH$_3$ | —CH=CH$_2$ | POM | 1.20s9H, 1.55s3H, 2.2–2.8m2H, 3.00d(2Hz)1H, 3.6–4.1m1H, (4.12d + 4.58d)ABq(8Hz)2H 5.0–6.2m4H, 5.77d(2Hz)2H. | | 33 |
| 4 | b-CH$_3$ | —CH=CH$_2$ | POM | 1.20s9H, (1.62s + 1.63s)3H, 2.3–2.8m2H, 3.2–3.4m1H, 3.6–4.1m1H, (4.17d + 4.40d)ABq(8Hz)2H, 5.0–6.2m4H, 5.80d(2Hz)2H. | | 33 |
| | | | | (Part 2) | | |
| 5 | a-CH$_3$ | —CH=CH$_2$ | ONB | 1.55s3H, 2.2–2.8m2H, 3.17d(2Hz)1H, 3.7–6.1m7H, (4.10d + 4.67d)ABq(8Hz)2H, 7.3–8.2m4H. | | 11 |
| 6 | a-CH$_3$ | —CH=CH$_2$ | PNB | 1.52s3H, 2.2–2.8m2H, 3.2m1H, 2.6–6.2m7H, (4.13d + 4.70d)ABq(9Hz)2H, (7.53d + 8.20d)q(8Hz)4H. | | 14 |
| 7 | b-CH$_3$ | —CH=CH$_2$ | PNB | 1.62s3H, 2.2–2.8m2H, 3.28m1H, 3.6–6.2m7H, (4.13d + 4.37d)ABq(9Hz)2H, (7.57d + 8.20d)q(8Hz)4H. | | 14 |
| 8 | a-H | —CO—CH$_3$ | PNB | | | 13 |
| 9 | b-H | —CO—CH$_3$ | PNB | | | 13 |
| | | | | (Part 3) | | |
| 10 | a-CH$_3$ | —CH=CH$_2$ | H | 1.60s3H, 2.4–2.8m2H, 3.22d(2Hz)1H, 3.7–4.1m1H, (4.13d + 4.67d)ABq(8Hz)2H, 5.0–6.2m4H, 8.7br1H. | | 10 |
| 11 | b-CH$_3$ | —CH=CH$_2$ | H | 1.63s3H, 2.3–2.8m2H, 3.22d(2Hz)1H, 3.7–4.1m1H, (4.15d + 4.47d)ABq(9Hz)2H, 5.0–6.2m4H. | | 10 |

TABLE E

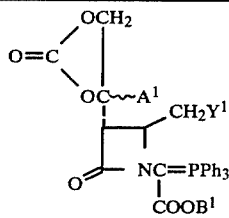

| No. | $A^1$ | $Y^1$ | $B^1$ | NMR:$\delta_{ppm}^{CDCl_3}$ (Hz value = J value) | IR: $\nu_{max}^{CHCl_3}$ | Ex. No. |
|---|---|---|---|---|---|---|
| | | | | (Part 1) | | |
| 1 | a-H | —CH=CH$_2$ | PNB | | 1815, 1750, 1355. | 12 |
| 2 | b-H | —CH=CH$_2$ | PNB | | 1810, 1750, 1355. | 12 |

TABLE E-continued
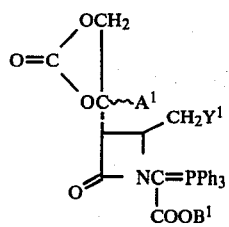
| No. | $A^1$ | $Y^1$ | $B^1$ | NMR: $\delta_{ppm}^{CDCl_3}$ (Hz value = J value) | IR: $\nu_{max}^{CHCl_3}$ | Ex. No. |
|---|---|---|---|---|---|---|
| 3 | a-H | —CH=CH$_2$ | POM | | 1820, 1750, 1640. | 15 |
| 4 | a-CH$_3$ | —CH=CH$_2$ | POM | | 1800, 1740. | 16 |
(Part 2)
| 5 | b-CH$_3$ | —CH=CH$_2$ | POM | | 1800, 1740. | 16 |
| 6 | a-CH$_3$ | —CH=CH$_2$ | ONB | | 1800, 1740. | 17 |
| 7 | a-CH$_3$ | —CH=CH$_2$ | PNB | | 1810, 1745, 1350. | 14 |
| 8 | b-CH$_3$ | —CH=CH$_2$ | PNB | | 1805, 1745, 1350. | 14 |
| 9 | a-CH$_3$ | —CO—CH$_3$ | PNB | | 1800, 1740. | 13 |
| 10 | b-CH$_3$ | —CO—CH$_3$ | PNB | | 1800, 1740. | 13 |
(Part 3)
| 11 | a-CH$_3$ | —CO—OH | PNB | | 1805, 1750, 1720, 1630. | 29 |
| 12 | a-CH$_3$ | —CO—SCH=HNCH—COCH$_3$ | PNB | | 1805, 1755, 1630. | 23 |
| 13 | a-CH$_3$ | —COOH | PNB | Phosphonium salt (Trifluoroacetate addition salt) | 1810, 1775, 1750, 1710, 1610, 1520. | 29 |

TABLE F

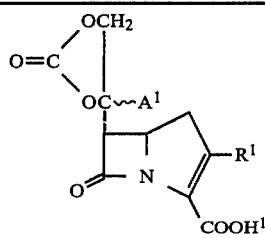

| No. | A¹ | R¹ | B¹ | NMR:$\delta_{ppm}^{CDCl_3}$ (Hz valve = J value) | IR:$\nu_{max}^{CHCl_3}$ | Ex. No. |
|---|---|---|---|---|---|---|
| | | | | (Part 1) | | |
| 1 | a-H | H | PNB | mp. 172–174° C. | | 18 |
| 2 | b-H | H | PNB | (2.90d + 3.05d)dd(3Hz)2H, (3.53d + 3.67d)dd(3Hz)1H, 4.5–5.3m4H, 5.33d(2Hz)2H, 6.60t(2Hz)1H, 7.53d + 8.18d)q(8Hz)4H. | 1360, 1785, 1820. | 18 |
| 3 | a-H | H | POM | 1.17s9H, 2.8–3.07m2H, 3.60–3.87m1H, 4.03–4.80m3H, 4.93–5.30m1H, 5.80s2H, 6.47–6.67m1H. | 1750, 1790, 1820. | 19 |
| 4 | a-CH₃ | H | POM | 1.22s9H, 1.62s3H, 3.00dt(2;9Hz)2H, 3.63d(3Hz)1H, (4.23d + 4.65d)ABq(9Hz)2H, 4.33dt(3;9Hz)1H, 5.87bs2H, 6.60t(2Hz)1H. | 1750, 1790, 1810. | 20 |
| | | | | (Part 2) | | |
| 5 | b-CH₃ | H | POM | 1.22s9H, 1.68s3H, 2.96dt(9;2.5Hz)2H, 3.57d(3Hz)1H, 4.1–4.5m1H, (4.19d + 4.4Sd)ABq(9Hz)2H, 5.86brs2H, 6.57t(2.5Hz)1H. | | 20 |
| 6 | a-CH₃ | H | PNB | 1.65s3H, 3.00t(2.5Hz)2H, 3.61d(3Hz)1H, (4.26d + 4.69d)ABq(9Hz)2H, 4.37dt(3;9Hz)1H, (5.35d + 5.42d)ABq(14Hz)2H, 6.64t(2.5Hz)1H, (7.59d + 8.23d)q(9Hz)4H. | 1730, 1788, 1820. | 21 |
| 7 | b-CH₃ | H | PNB | 1.70s3H, 2.94dt(2;9Hz)2H, 3.58d(3Hz)1H, (4.22d + 4.47d)ABq(9Hz)2H, 4.32dt(3;9Hz)1H, (5.23d + 5.52d)ABq(14Hz)2H, 6.62t(2Hz)1H, (7.60d + 8.25d)q(9Hz)4H. | | 21 |
| 8 | a-CH₃ | H | ONB | | | 22 |
| 9 | a-CH₃ | CH₃ | PNB | 1.60s3H, 2.17s3H, 2.92d(8Hz)2H, 3.47d(3Hz)1H, 4.13m1H, (4.20d + 4.70d)ABq(9Hz)2H, (5.22d + 5.37d)ABq(14Hz)2H, 7.63d + 8.23d)q(9Hz)4H. | 1775, 1805. | 24 |
| | | | | (Part 3) | | |
| 10 | b-CH₃ | CH₃ | PNB | 1.70s3H, 2.17s3H, 2.97d(8Hz)2H, 3.60d(3Hz)1H, 4.03m1H, (4.26d + 4.50d)ABq(9Hz)2H, (5.23d + 5.55d)ABq(14Hz)2H, (7.60d + 8.23d)q(9Hz)4H. | | 24 |
| 11 | a-CH₃ | CH₃ | POM | 1.23s9H, 1.67s3H, 2.17s3H, 2.92d(10Hz)2H, 3.47d(2Hz)1H, 4.10m1H, (4.20d + 4.67d)ABq(9Hz)2H, 5.90m2H. | 1750, 1800. | 34 |
| 12 | a-CH₃ | —SO—CH₃ | PNB | 1.67s3H, 3.1–3.7m2H, 3.90d(3.5Hz)1H, 4.2–4.6m1H, (4.27d + 4.71d)ABq(8.5Hz)2H, (5.26d + 5.51d)ABq(13Hz)2H, (7.60d + 8.23d)q(8Hz)4H. | | 39 |
| 13 | a-CH₃ | —SO—CH₂—CH₂—NH—CO—CH₃ | PNB | 1.63s3H, 1.97s3H, 2.6–3.9m7H, 4.2–4.6m1H, (4.22d + 4.65d)ABq(8.5Hz)2H, (5.20d + 5.53d)ABq(10Hz)2H, 6.58m1H, (7.53d + 8.19d)q(8.5Hz)4H. | 1675, 1745, 1790, 1810. | 42 |
| | | | | (Part 4) | | |
| 14 | a-CH₃ | —S—CH=CH—NH—CO—CH₃ | PNB | 1.66s3H, 2.08s3H, 3.18brd(9Hz)2H, 3.55d(2.5Hz)1H, 4.0–4.4m1H, (4.21d + 4.65d)ABq(9Hz)2H, 5.19d + 5.50d)ABq(13Hz)2H, 5.83d(14Hz)1H, 4.93brd(14Hz)1H, (7.53d + 8.19d)q(8.5Hz)4H. | 1706, 1785, 1805. | 23 |

TABLE F-continued

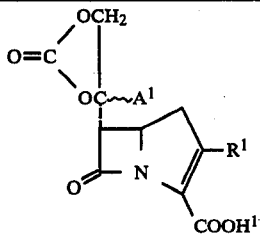

| No. | $A^1$ | $R^1$ | $B^1$ | NMR: $\delta_{ppm}^{CDCl_3}$ (Hz valve = J value) | IR: $\nu_{max}^{CHCl_3}$ | Ex. No. |
|---|---|---|---|---|---|---|
| 15 | a-CH$_3$ | —S—CH$_2$—CH$_2$—NH—CO—CH$_3$ | POM | 1.22s9H, 1.63s3H, 1.98s3H, 2.8–3.7m6H, 4.1–4.5m1H, (4.19d + 4.63d)ABq(9Hz)2H, (5.80d + 5.97d)ABq(5.5Hz)2H, 6.45brt(5Hz)1H. | 1675, 1790, 1810. | 43 |
| 16 | b-CH$_3$ | —S—CH$_2$—CH$_2$—NH—CO—CH$_3$ | PNB | 1.69s3H, 1.97s3H, 2.7–3.8m6H, 3.67d (3Hz)1H, 4.0–4.5m1H, (4.21d + 4.46d)ABq (9Hz)2H, (5.18d + 5.22d)ABq(14Hz)2H, 6.40brt(6Hz)1H, (7.60d + 8.18d)q(9Hz)4H. | 3455, 3975, 1808, 1785, 1705, 1680. | 45 |

(Part 5)

| 17 | b-CH$_3$ | —S—CH=CH—NH—CO—CH$_3$ | PNB | 1.70s3H, 2.03s3H, 3.19brd(9Hz)2H, 3.65d (3Hz)1H, 4.0–4.4m1H, (4.22d + 4.41d)ABq (8Hz)2H, (5.18d + 5.50d)ABq(14Hz)2H, 5.86d (14Hz)1H, 7.13dd(14Hz;10Hz)1H, (7.57d + 8.13d)q(8Hz)4H, 8.43brd(10Hz)1H. (CDCl$_3$ + CD$_3$CN) | | 56 |

TABLE G

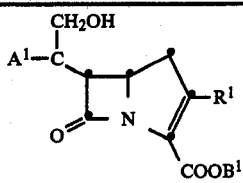

| No. | $A^1$ | $R^1$ | $B^1$ | NMR: $\delta_{ppm}^{CDCl_3}$ (Hz value = J value) | IR: $\nu_{max}^{CHCl_3}$ | Ex. No. |
|---|---|---|---|---|---|---|
| (Part 1) | | | | | | |
| 1 | H | H | POM | 1.23s9H, 2.78–3.10m2H, 4.33–4.62m2H, 4.70–5.78m1H, (5.85d + 5.98d)ABq(5Hz)2H, 6.32–6.65m2H. | 1750, 1790, 3400. | 46 |
| 2 | H | H | PNB | (2.88d + 3.05d)dd(3Hz,',4.4–5.3m3H, 5.40d(3Hz)2H, 6.3–6.7mH, (7.68d + 8.28d) q(8Hz)4H. | 1360, 1735, 1780, 3450. | 47 |
| 3 | CH$_3$ | H | POM | 1.23s9H, 1.83s3H, (2.83d + 2.92d)dd(3Hz) 2H, 3.27brs1H, 4.40s2H, 4.62brt(9Hz)1H, 5.90brs2H, 6.58t(3Hz)1H. | 1615, 1760, 2975, 3430. | 48 (1) |
| 4 | CH$_3$ | H | PNB | 2.04s3H, 2.27brs1H, (2.85d + 3.00d)dd (2.5;9Hz)2H, 4.32s2H, 5.04brt(9Hz)1H, (5.26d + 5.55d)ABq(14Hz)2H, 6.58t(2.5Hz) 1H, (7.67d + 8.28d)q(9Hz)4H. | | 48 (1) |
| (Part 2) | | | | | | |
| 5 | CH$_3$ | CH$_3$ | PNB | 1.93s3H, 2.03s3H, 2.80d(8Hz)2H, 4.20s 2H, 4.83m1H, (5.21d + 5.54d)ABq(13.5Hz) 2H, (7.67d + 8.20d)q(9Hz)4H. | | 50 |

TABLE G-continued

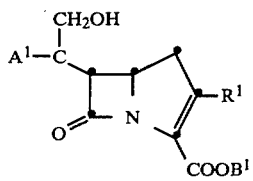

| No. | $A^1$ | $R^1$ | $B^1$ | NMR: $\delta_{ppm}^{CDCl_3}$ (Hz value = J value) | IR: $\nu_{max}^{CHCl_3}$ | Ex. No. |
|---|---|---|---|---|---|---|
| 6 | $CH_3$ | $CH_3$ | POM | 1.23s9H, 1.67s3H, 2.06m3H, 2.92d(10Hz) 2H, 4.25s2H, 4.75m1H, 5.93m1H. | | 49 |
| 7 | $CH_3$ | $\overset{O}{\underset{\beta}{\uparrow}}$<br>$-S$<br>$\|$<br>$CH_3$ | PNB | 2.03s3H, 2.79s3H, 3.2–3.6m2H, 4.32brs 2H, 5.14brt(9Hz)1H, (5.23d + 5.53d)ABq (12Hz)2H, (7.63d + 8.22d)q(9Hz)4H. | 1600, 1760, 3350. | 51 41 40 |
| 8 | $CH_3$ | $\overset{O}{\underset{\alpha}{\uparrow}}$<br>$-S$<br>$\|$<br>$CH_3$ | PNB | 2.08s3H, 2.83s3H, 3.5–3.8m2H, 5.30brt (9Hz)1H, (5.39d + 5.68d)ABq(14Hz)2H, (7.86d + 8.18d)q(9Hz)4H. | 1600, 1775, 3350. | 41 |
| 9 | $CH_3$ | $-S$<br>$\|$<br>$CH$<br>$\|\|$<br>$CH$<br>$\|$<br>$NH$<br>$\|$<br>$CO$<br>$\|$<br>$CH_3$ | PNB | 2.01s3H, 2.08s3H, 3.11d(8.5Hz)2H, 4.29s 2H, 4.89brt(8.5Hz)1H, (5.19d + 5.57d)ABq (14Hz)2H, 5.86d(13.5Hz)1H, 7.20dd(10.5; 13.5Hz)1H, 7.48 brd(10.5Hz)1H, (7.67d + 8.23d)q((9Hz)4H. | 1625, 1705, 1755, 3410. | 55 |

(Part 3)

| No. | $A^1$ | $R^1$ | $B^1$ | NMR: $\delta_{ppm}^{CDCl_3}$ (Hz value = J value) | IR: $\nu_{max}^{CHCl_3}$ | Ex. No. |
|---|---|---|---|---|---|---|
| 10 | $CH_3$ | $-S$<br>$\|$<br>$CH_2$<br>$\|$<br>$CH_2$<br>$\|$<br>$NH$<br>$\|$<br>$CO$<br>$\|$<br>$CH_3$ | PNB | 1.95s3H, 2.02s3H, 2.6–3.6m6H, 4.29s2H, 5.01brt(9Hz)1H, (5.18d + 5.56d)ABq(14Hz) 2H, (7.67d + 8.18d)q(9Hz)4H, (CDCl$_3$ + C$_5$D$_5$N) | 3355, 3300, 2925, 1750, 1705, 1695, 1655 (KBr). | 52 53 |
| 11 | $CH_3$ | $-S$<br>$\|$<br>$CH_2$<br>$\|$<br>$CH_2$<br>$\|$<br>$NH$<br>$\|$<br>$CO$<br>$\|$<br>$CH_3$ | POM | 1.23s9H, 1.98s6H, 2.6–3.7m6H, 4.25brs 2H, 4.92brt(8.5Hz)1H, (5.83d + 5.94d) ABq(5Hz)2H, 6.4–6.7m1H. | 1670, 1710, 1755. | 54 |
| 12 | $CH_3$ | 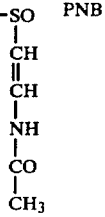$-SO$<br>$\|$<br>$CH$<br>$\|\|$<br>$CH$<br>$\|$<br>$NH$<br>$\|$<br>$CO$<br>$\|$<br>$CH_3$ | PNB | | | 55 |

(Part 4)

TABLE G-continued

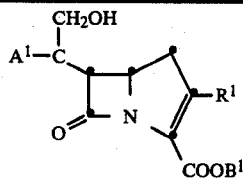

| No. | A¹ | R¹ | B¹ | NMR:$\delta^{CDCl_3}_{ppm}$ (Hz value = J value) | IR: $\nu^{CHCl_3}_{max}$ | Ex. No. |
|---|---|---|---|---|---|---|
| 13 | CH₃ | —SCH=NHCH—COCH₃ | Na | 1.98s3H, 2.06s3H, 3.10d(9Hz)2H, 4.22s 2H, 4.8–5.0m1H, 6.01d(14Hz)1H, 7.13d (14Hz)1H. (D₂O) | | 58 |

TABLE H

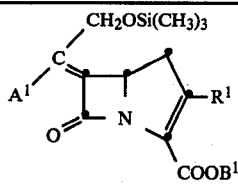

| No. | A¹ | R¹ | B¹ | NMR: $\delta^{CDCl_3}_{ppm}$ (Hz value = J value) | IR: $\nu^{CHCl_3}_{max}$ | Ex. No. |
|---|---|---|---|---|---|---|
| 1 | CH₃ | H | POM | 0.17s9H, 1.23s9H, 1.98s3H, (2.78d + 2.93d) dd(3Hz)2H, 4.20brs2H, 4.93bt(9Hz)1H, 5.87s2H, 6.48t(3Hz)1H. | | 48 (1) |
| 2 | CH₃ | H | PNB | 0.18s9H, 2.02s3H, (2.80d + 2.95d)dd (2.5Hz)2H, 4.23s2H, 5.00bt1H, (5.25d + 5.54d)ABq(14Hz)2H, 6.54t(2.5Hz)1H, (7.64d + 8.25d)q(9Hz)4H. | | 48 (1) |
| 3 | CH₃ | —S—CH₂—CH₂—NH—CO—CH₃ | PNB | 0.18s9H, 1.80s6H, 2.7–3.7m6H, 4.23s2H, 4.91brt(9Hz)1H, 5.21d + 5.61d)ABq(14Hz) 2H, 6.0–6.4m1H, (7.71d + 8.25d)q4H. | 1675, 1700 (sh), 1750. | 53 |

(Part 2)

| 4 | CH₃ | —S—CH₂—CH₂—NH—CO—CH₃ | POM | 0.18s9H, 1.23s9H, 2.00brs3H, 4.21s2H. | | 54 |

TABLE J

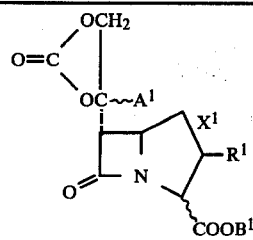

| No. | A¹ | R¹ | B¹ | X¹ | NMR:$\delta^{CDCl_3}_{ppm}$ (Hz value = J value) | IR:$\nu^{CHCl_3}_{max}$ | Ex. No. |
|---|---|---|---|---|---|---|---|

(Part 1)

TABLE J-continued

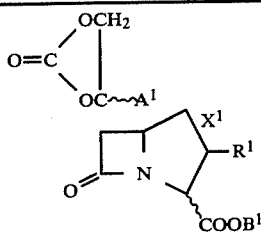

| No. | A¹ | R¹ | B¹ | X¹ | NMR:$\delta_{ppm}^{CDCl_3}$ (Hz value = J value) | IR:$\nu_{max}^{CHCl_3}$ | Ex. No. |
|---|---|---|---|---|---|---|---|
| 1 | a-CH₃ | β-—S—CH₃ | β-PNB | H | 1.61s3H, 2.14s3H, 3.40d(2.5Hz)1H, 3.6–4.1m2H, (4.17d + 4.64d)ABq(9Hz)2H, 4.27d(7Hz)1H, 5.32s2H, (7.55d + 8.19d)q (8.5Hz)4H. | | 38 |
| 2 | a-CH₃ | β-—S—CH₃ | β-PNB | H | 1.63s3H, 2.17s3H, 3.45d(2.5Hz)1H, 3.6–4.1m2H, (4.20d + 4.65d)ABq(8.5Hz)2H, 4.54d(5.5Hz)1H, 5.30s2H, (7.53d + 7.90d)q(8.5Hz)4H. | | 38 |

(Part 2)

| No. | A¹ | R¹ | B¹ | X¹ | NMR:$\delta_{ppm}^{CDCl_3}$ (Hz value = J value) | IR:$\nu_{max}^{CHCl_3}$ | Ex. No. |
|---|---|---|---|---|---|---|---|
| 3 | a-CH₃ | α-—S—CH₃ | α-PNB | H | 1.64s3H, 2.17s3H, 2.2–2.4m2H, 3.33d (2.5Hz)1H, 3.4–3.8m1H, 4.0–4.4m1H, (4.19d + 4.64d)ABq(8Hz)2H, 4.89d(7Hz)1H, 5.31s2H, (7.56d + 8.24d)q(8.5Hz)4H. | | 38 |
| 4 | a-CH₃ | β-—SO—CH₃ | β-PNB | α-Cl | 1.63s3H, 2.4–2.9m2H, 2.80s3H, 3.58d (2.5Hz)1H, 4.1–4.5m1H, (4.23d + 4.68d) ABq(9Hz)2H, 5.33s2H, (7.55d + 8.20d)q (8Hz)4H. | | 39 41 |
| 5 | a-CH₃ | α-—SO—CH₃ | α-PNB | β-Cl | 1.63s3H, 2.47dd(2;15Hz)1H, 2.85s3H, 3.14dd(9;15Hz)1H, 3.82d(3Hz)1H, (4.16d + 4.68d)ABq(9Hz)2H, 4.36brd(9Hz)1H, 5.15s1H, 5.30s2H,(7.59d + 8.27d)q(9Hz)4H. | | 37 |

(Part 3)

| No. | A¹ | R¹ | B¹ | X¹ | NMR:$\delta_{ppm}^{CDCl_3}$ (Hz value = J value) | IR:$\nu_{max}^{CHCl_3}$ | Ex. No. |
|---|---|---|---|---|---|---|---|
| 6 | a-CH₃ | β-—S—CH₂—CH₂—NH—CO—CH₃ | β-PNB | H | 1.58s3H, 1.96s3H, (2.1–3.0m + 3.2–3.6m) 6H, 3.38d(2.5Hz)1H, 3.6–4.0m2H, 4.26d (7.5Hz)1H, (4.19d + 4.65d)ABq(9Hz)2H, 5.32s2H, 6.2Sbrt(5Hz)1H, (7.62d + 8.02d) q(8.5Hz)4H. | 1670, 2960, 1805, 1700, 1740, 3435. | 37 40 |
| 7 | a-CH₃ | β-—S—CH₂—CH₂—NH—CO—CH₃ | α-PNB | H | 1.62s3H, 1.98s3H, 2.3–3.7m6H, 3.48d (2Hz)1H, 3.7–4.2m2H, (4.22d + 4.66d)ABq (9Hz)2H, 4.53d(5Hz)1H, 5.31s2H, 6.37 brt(6Hz)1H, (7.55d + 8.22d)q(9Hz)4H. | 44 | 37 |
| 8 | a-CH₃ | α-—S—CH₂—CH₂—NH—CO—CH₃ | α-PNB | H | 1.58s3H, 1.93s3H, (2.1–2.9m + 3.2–3.8m) 7H, 3.38d(3Hz)1H, 3.9–4.4m1H, (4.20d + 4.62d)ABq(9Hz)2H, 4.53d(7Hz)1H, 5.30s2H, 6.32brt(5Hz)1H, (7.56d + 8.23d) q(9Hz)4H. | | 37 |

(Part 4)

TABLE J-continued

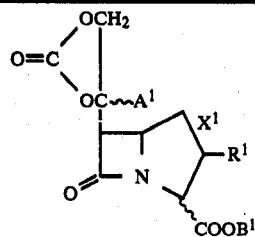

| No. | $A^1$ | $R^1$ | $B^1$ | $X^1$ | NMR:$\delta_{ppm}^{CDCl_3}$ (Hz value = J value) | IR:$\nu_{max}^{CHCl_3}$ | Ex. No. |
|---|---|---|---|---|---|---|---|
| 9 | a-$CH_3$ | α-SO—$CH_2$—$CH_2$—NH—CO—$CH_3$ | β-PNB | β-Cl | 1.62s3H, 1.98s3H, 3.82d(3Hz)1H, (4.19d + 4.67d)ABq(8.5Hz)2H, 5.17s1H, 5.28s 2H, 6.38m1H, (7.51d + 8.17d)q(5.5Hz)4H. | 1730, 2960, 1800, 1770, 3430, 1660. | 42 |
| 10 | a-$CH_3$ | ξ—S—$CH_2$—$CH_2$—NH—CO—$CH_3$ | ξ-POM | H | 1.23s9H, 1.60s3H, 2.00s3H, (4.22 + 4.66d)ABq(9Hz)2H, 5.83s2H, 6.3–6.8m1H. | 1670, 1770, 1810. | 36 |
| 11 | b-$CH_3$ | $R^1 + X^1$ = OXO | PNB | | | 1807, 1765, 1700. | 2S |

TABLE K

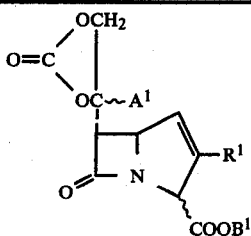

| No. | $A^1$ | $R^1$ | $B^1$ | NMR:$\delta_{ppm}^{CDCl_3}$ (Hz value = J value) | IR:$\nu_{max}^{CHCl_3}$ | Ex. No. |
|---|---|---|---|---|---|---|
| 1 | a-$CH_3$ | —S—$CH_2$—$CH_2$—NH—CO—$CH_3$ | α-PNB | 1.63s3H, 1.98s3H, 2.5–3.7m4H, 3.41d (3Hz)1H, (4.22d + 4.69d)ABq(8.5Hz)2H, 4.5–4.8m1H, 5.18m1H, 5.33s2H, 6.13t (1.5Hz)1H, 6.31brt(6Hz)1H, (7.58d 8.22d)q(9Hz)1H. | 1675, 1750sh, 1780, 1810. | 44 |
| 2 | a-$CH_3$ | —S—$CH_2$—$CH_2$—NH—CO—$CH_3$ | α-POM | 1.23s9H, 1.63s3H, 2.00s3H, 2.5–3.6m5H, (4.19d + 4.64d)ABq(8.5Hz)2H, 4.4–4.5m1H, 5.1m1H, 5.81brs2H, 6.06brs1H, 6.1–6.6m1H. | 1670, 1780, 1810. | 43 |

TABLE L

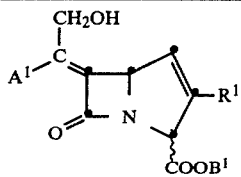

| No. | $A^1$ | $R^1$ | $B^1$ | NMR:$\delta_{ppm}^{CDCl_3}$ (Hz value = J value) | IR:$\nu_{max}^{CHCl_3}$ | Ex. No. |
|---|---|---|---|---|---|---|
| 1 | a-$CH_3$ | —S—$CH_2$—$CH_2$—NH—CO—$CH_3$ | POM | 1.22s9H, 1.9Ss6H, 2.4–3.9m4H, 4.25brs 2H, 5.0–5.3m2H, (5.74d + 5.88d)ABq(5.5Hz) 2H, 6.18brs1H, 6.2–6.6m1H. | 1670, 1755. | 54 |

TABLE M

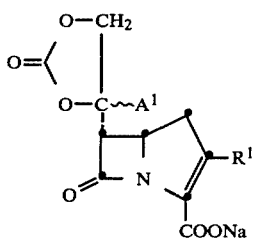

| No. | $A^1$ | $R^1$ | UV:$\lambda_{max}^{CH_3OH}$ nm | Ex. No. |
|---|---|---|---|---|
| 1 | a-$CH_3$ | $CH_3$ | 265 nm | 34 |
| 2 | b-$CH_3$ | $CH_3$ | 265 nm | 35 |
| 3 | b-$CH_3$ | —SCH=NHCH—COCH$_3$ | NMR: $\delta^{D_2O}$ 1.63s3H, 2.03s3H, 3.13d(9Hz)2H, 3.S2d(2Hz)1H, 4.0–4.4m1H, 4.47brd2H, 6.00 d(14Hz)1H, 7.15d(14Hz)1H. | 57 |

What we claim is:

1. A carbapenem compound of the formula

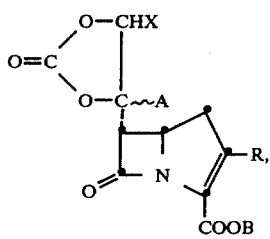

wherein
A is hydrogen or 1 to 3C alkyl,
B is a conventional carboxy-protecting ester conventional in the beta-lactam chemistry or alkali metal or alkaline earth metal salt group,
R is hydrogen, hydroxy, 1 to 3C alkyl, 1 to 3C alkylthio, 1 to 3C alkylsulfinyl, 3 to 6C alkanoylaminoalkylthio, 3 to 6C alkanoylaminoalkylsulfinyl, 4 to 7C alkanoylaminoalkenylthio or 4 to 7C alkanoylamino alkenylsulfinyl,
X is hydrogen or 1 to 3C alkyl, and
the wave line shows either R or S bond.

2. A compound as claimed in claim 1 wherein X is hydrogen.

3. A compound as claimed in claim 1 wherein X is methyl.

4. A compound as claimed in claim 2 wherein A is hydrogen.

5. A compound as claimed in claim 2 wherein A is methyl.

6. A compound as claimed in claim 1 wherein B is hydrogen, sodium, p-nitrobenzyl, o-nitrobenzyl, pivaloyloxymethyl, diphenylmethyl, phthalidyl or phenyl.

7. A compound as claimed in claim 1 wherein R is hydrogen, hydroxy, methyl, methylthio, methylsulfinyl, acetamidoethylthio, acetoamidoethylsulfinyl, acetamidovinylthio or acetamidovinylsulfinyl.

8. A compound as claimed in claim 4 wherein R is hydrogen and B is hydrogen, sodium, p-nitrobenzyl or pivaloyloxymethyl.

9. A compound as claimed in claim 5 wherein R is hydrogen and B is hydrogen, sodium, p-nitrobenzyl, o-nitrobenzyl or pivaloyloxymethyl.

10. A compound as claimed in claim 5 wherein R is methyl and B is hydrogen, sodium, p-nitrobenzyl, or pivaloyloxymethyl.

11. A compound as claimed in claim 5 wherein R is ethylthio and B is hydrogen, sodium, p-nitrobenzyl.

12. A compound as claimed in claim 5 wherein R is methylsulfinyl and B is hydrogen, sodium, p-nitrobenzyl or diphenylmethyl.

13. A compound as claimed in claim 5 wherein R is acetamidoethylthio and B is hydrogen, sodium, p-nitrobenzyl or pivaloyloxymethyl.

14. A compound as claimed in claim 5 wherein R is acetamidoethylsulfinyl and B is hydrogen, p-nitrobenzyl or pivaloyloxymethyl.

15. A compound as claimed in claim 5 wherein R is acetamidovinylthio and B is hydrogen, sodium, p-nitrobenzyl or pivaloyloxymethyl.

16. A compound as claimed in claim 5 wherein R is acetamidovinylsulfinyl and B is hydrogen, sodium, p-nitrobenzyl or pivaloyloxymethyl.

* * * * *